(12) United States Patent
Ackland

(10) Patent No.: US 11,415,573 B2
(45) Date of Patent: Aug. 16, 2022

(54) DIAGNOSTICS

(71) Applicant: Queen Mary University of London, London (GB)

(72) Inventor: Gareth Ackland, London (GB)

(73) Assignee: QUEEN MARY UNIVERSITY OF LONDON, London (GB)

(*) Notice: Subject to any disclaimer, the term of this patent is extended or adjusted under 35 U.S.C. 154(b) by 0 days.

(21) Appl. No.: 15/324,316

(22) PCT Filed: Jul. 8, 2015

(86) PCT No.: PCT/GB2015/051986
§ 371 (c)(1),
(2) Date: Jan. 6, 2017

(87) PCT Pub. No.: WO2016/005753
PCT Pub. Date: Jan. 14, 2016

(65) Prior Publication Data
US 2017/0184570 A1 Jun. 29, 2017

(30) Foreign Application Priority Data
Jul. 8, 2014 (GB) .................. 1412131

(51) Int. Cl.
*G01N 33/50* (2006.01)
*C12Q 1/26* (2006.01)
*C12Q 1/00* (2006.01)
*G01N 33/68* (2006.01)

(52) U.S. Cl.
CPC ......... *G01N 33/5047* (2013.01); *C12Q 1/005* (2013.01); *C12Q 1/26* (2013.01); *G01N 33/6812* (2013.01); *G01N 2800/24* (2013.01); *G01N 2800/26* (2013.01)

(58) Field of Classification Search
CPC ...... C12Q 1/26; C12Q 1/005; G01N 33/5047; G01N 33/6812; G01N 2800/24; G01N 2800/26
See application file for complete search history.

(56) References Cited

U.S. PATENT DOCUMENTS

| 4,614,714 A | 9/1986 | Kusakabe et al. |
| 4,623,626 A | 11/1986 | Kusakabe et al. |
| 2008/0213751 A1 | 9/2008 | Schmolz et al. |
| 2009/0104596 A1 | 4/2009 | Assadi-Porter et al. |
| 2013/0244899 A1 | 9/2013 | McNulty et al. |

FOREIGN PATENT DOCUMENTS

| DE | 272478 | 10/1989 |
| DE | 10 2006 062398 A1 | 6/2008 |
| JP | 2006-153637 | 6/2006 |
| WO | WO 2003/087801 | 10/2003 |
| WO | WO 2004/048603 | 6/2004 |
| WO | WO 2008/081193 | 7/2008 |
| WO | WO 2013/040099 A2 | 3/2013 |
| WO | WO 2014/087137 | 6/2014 |

OTHER PUBLICATIONS

Dale et al (Purinergic Signalling 8(1), S27-S40) (Year: 2012).*
Spranger et al (Year: 1996).*
Thomas et al (Year: 2013).*
Schmolz et al (DE102006062398A1, published Jun. 26, 2006, Machine Translation) (Year: 2006).*
O'Neill et al (Year: 2004).*
O'Neill (Year: 2004).*
Thomas (Year: 2013).*
Schmolz (Year: 2006).*
Block (Year: 2007).*
Spranger (Year: 1996).*
Dale (Year: 2012).*
Jabs et al (Year: 1995).*
Gaieski et al (Year: 2013).*
Tian (Year: 2007).*
Dou (Year: 2007).*
Romero (Year: 2010).*
Jabs (Year: 1995).*
Berg et al. "Effects of lipopolysaccharide infusion on arterial levels and transcerebral exchange kinetics of glutamate and glycine in healthy humans," Acta Pathalogica, Microbiologica et Immunologica Scandinavica, 2012, vol. 120, pp. 761-766.
Chen et al. "Measurement of Oxidative Burst in Neutrophils," Methods Mol Biol., 2012, vol. 844, pp. 115-124.
Chiarla et al. "The Relationship between Plasma Taurine and Other Amino Acid Levels in Human Sepsis," The Journal of Nutrition, Sep. 2000, vol. 130, No. 9, pp. 2222-2227.
Dale et al. "Listening to the brain: microelectrode biosensors for neurochemicals," Trends in Biotechnology, Aug. 2005, vol. 23, No. 8, pp. 420-428.
Dale et al. "Measurement of purine release with microelectrode biosensors," Purinergic Signalling, 2012, vol. 8, Suppl. 1, pp. S27-S40.
Farthing et a. "An HPLC method for determination of inosine and hypoxanthine in human plasma from healthy volunteers and patients presenting with potential acute cardiac ischemia," Journal of Chromatography B, 2007, vol. 854, pp. 158-164.
Farthing et al. "A rapid and simple chemiluminescence method for screening levels of inosine and hypoxanthine in non-traumatic chest pain patients," Luminescence, Jan. 2011, vol. 26, pp. 65-75.
Frenguelli et al. "Temporal and mechanistic dissociation of ATP and adenosine release during ischaemia in the mammalian hippocampus," Journal of Neurochemistry, 2007, vol. 101, pp. 1400-1413.

(Continued)

*Primary Examiner* — Jeffrey S Lundgren
*Assistant Examiner* — Ibrahim D Bori
(74) *Attorney, Agent, or Firm* — Sheridan Ross P.C.

(57) ABSTRACT

The present invention relates to the detection or diagnosis of infection or inflammation in a patient. In particular, the invention provides methods that allow the detection of markers in a sample from a patient or subject, such as a blood sample, which will indicate whether the patient or subject has an infection or has an inflammatory response.

11 Claims, 10 Drawing Sheets

(56) References Cited

OTHER PUBLICATIONS

Gourine et al. "Release of ATP and glutamate in the nucleus tractus solitarii mediate pulmonary stretch receptor (Breuer-Hering) reflex pathway," The Journal of Physiology, 2008, vol. 586, No. 16, pp. 3963-3978.
Hasko et al. "Adenosine: an endogenous regulator of innate immunity," Trends in Immunology, Jan. 2004, vol. 25, No. 1, pp. 33-39.
Heinrich et al. "K+ depolarization evokes ATP, adenosine and glutamate release from glia in rat hippocampus: a microelectrode biosensor study," British Journal of Pharmacology, 2012, vol. 167, pp. 1003-1020.
Junger "Immune cell regulation by autocrine purinergic signalling," Nat Rev Immunol., Mar. 2011, vol. 11, No. 3, pp. 201-212.
Lecka et al. "Extracellular-Purine Metabolism in Blood Vessels (Part I). Extracellular-Purine Level in Blood of Patients with Abdominal Aortic Aneurysm," Nucleosides, Nucleotides and Nucleic Acids, 2010, vol. 29, No. 9, pp. 647-657.
Llaudet et al. "A three-enzyme microelectrode sensor for detecting purine release from central nervous system," Biosensors & Bioelectronics, 2003, vol. 18, pp. 43-52.
Llaudet et al. "Microelectrode Biosensor for Real-Time Measurement of ATP in Biological Tissue," Analytical Chemistry, May 2005, vol. 77, No. 10, pp. 3267-3273.
Masse et al. "Purine-mediated signalling triggers eye development," Nature, Oct. 2007, vol. 449, No. 7165, pp. 1058-1062.
Mazzone et al. "Electrochemical detection of endogenous glutamate release from rat spinal cord organotypic slices as a real-time method to monitor excitotoxicity," Journal of Neuroscience Methods, 2011, vol. 197, pp. 128-132.
Miseta et al. "Relationship between cellular ATP, potassium, sodium and magnesium concentrations in mammalian and avian erythrocytes," Biochimica et Biophysica Acta, 1993, vol. 1175, pp. 133-139.
Murphy et al. "Measurement in Vitro of Human Plasma Glyceral with a Hydrogen Peroxide Detecting Microdialysis Enzyme Electrode," Anal. Chem. 1994, vol. 66, pp. 4345-4353.
Naum et al. "Platelets and ATP Prime Neutrophils for Enhanced O2-Generation at Low Concentrations but Inhibit O2-Generation at High Concentration," Journal of Leukocyte Biology, 1991, vol. 49, pp. 83-89.
Pohanka et al. "Electrochemical biosensors—principles and applications," Journal of Applied Biomedicine, 2008, vol. 6, pp. 57-64.
Ramakers et al. "How systemic inflammation modulates adenosine metabolism and adenosine receptor expression in humans in vivo," Critical Care Medicine, Jun. 2012, vol. 40, No. 9, pp. 2609-2616.
Ramakers et al. "Modulation of Innate Immunity by Adenosine Receptor Stimulation," Shock, Sep. 2011, vol. 36, No. 3, pp. 208-215.
Robinson et al. "Monitoring Rapid Chemical Communication in the Brain," Chem Rev. Jul. 2008, vol. 108, No. 7, pp. 2554-2584.
Shigetomi et al. "TRPA1 Channels Are Regulators of Astrocyte Basal Calcium Levels and Long-Term Potentiation via Constitutive D-Serine Release," The Journal of Neuroscience, Jun. 2013, vol. 33, No. 24, pp. 10143-10153.
Souba et al. "The Effects of Sepsis and Endotoxemia on Gut Glutamine Metabolism," Annals of Surgery, May 1990, vol. 211, No. 5, pp. 543-549.
Tian et al. "A microelectrode biosensor for real time monitoring of L-glutamate release," Analytica Chimica Acta, 2009, vol. 645, pp. 86-91.
Tian et al. "Ruthenium Purple-Mediated Microelectrode Biosensors Based on Sol-Gel Film," Analytical Chemistry, Sep. 2007, vol. 79, No. 17, pp. 6760-6766.
Vaughan et al. "Inhibition of Neutrophil Apoptosis by ATP Is Mediated by the P2Y11 Receptor," The Journal of Immunology, 2007, vol. 179, pp. 8544-8553.
Wilson et al. "In vivo biosensors," The FEBS Journal, 2007, vol. 274, pp. 5452-5461.
Wilson et al. "In-Vivo Electrochemistry: What Can We Learn about Living Systems?" Chem. Rev. 2008, vol. 108, No. 7, pp. 2462-2481.
Si Qin et al: "Microsensors for in vivo Measurement of Glutamate in Brain Tissue", Sensors, vol. 8, No. 11, Nov. 4, 2008; pp. 6860-6884.
C.R. Esther et al: "Extracellular purines are biomarkers of neutrophilic airway inflammation", European Respiratory Journal, vol. 31, No. 5, Jan. 9, 2008 (Jan. 9, 2008); pp. 949-956.
International Search Report and Written Opinion prepared by the European Patent Office dated Sep. 30, 2015, for International Application No. PCT/GB2015/051986.

* cited by examiner

DIAGNOSTICS

CROSS REFERENCE TO RELATED APPLICATIONS

This application is a national stage application under 35 U.S.C. 371 and claims the benefit of PCT Application No. PCT/GB2015/051986 having an international filing date of 8 Jul. 2015, which designated the United States, which PCT application claimed the benefit of Great Britain Application No. 1412131.3 filed 8 Jul. 2014, the disclosure of each of which are incorporated herein by reference.

FIELD OF THE INVENTION

The present invention relates to the detection or diagnosis of infection or inflammation in a patient. In particular, the invention provides methods that allow the detection of markers in a sample from a patient or subject, such as a blood sample, which will indicate whether the patient or subject has an infection or has an inflammatory response.

BACKGROUND TO THE INVENTION

There is a need to be able to diagnose immunosuppression and to be able to monitor the health of the immune system in normal individuals and in patients at risk of acquiring infections, both in hospital and the community. Current biomarkers are crude, non-specific and frequently lead to erroneous antibiotic use, which is associated with serious side-effects. Dynamic, real-time, easy to use tests performed by healthcare professionals at the bedside to enable immune function to be assessed in an objective fashion would enable focused, considered treatments including the rationale use of antibiotics 13 an urgent healthcare priority.

SUMMARY OF THE INVENTION

The present invention is based on the ability to detect molecules released by immune cells, both in their resting state and following stimulation. This permits the identification of characteristic patterns of immune response.

Accordingly, the invention provides a method of detecting infection or inflammation in a mammalian subject, the method comprising: (a) detecting the amount of at least one marker selected from glutamate, lactate, ATP, D-serine, acetylcholine and adenosine in a sample from said subject and (b) comparing the amount of the marker(s) of (a) with the amount of the same marker(s) in a control sample, wherein an increased or decreased amount of said marker(s) in the sample from the subject, when compared to the control sample, is indicative of the presence of inflammation or infection.

The methods of the invention may comprise contacting the sample with a stimulator of immune cells and determining whether said stimulus leads to any change in the amount of said marker(s) in the sample. The methods may comprise determining whether the said stimulus leads to a change in the amount of said marker(s) in the sample that is below or above a control value for the said change, such as a value for the change in a control sample. In such methods, the amount of said marker(s) may be tested within 5 minutes of contacting the sample with said stimulus In the methods of the invention any one or more of the following may apply:
the infection may be a pathogenic infection, a bacterial infection, a viral infection, a fungal infection and/or sepsis;
the sample may be an in vivo, in vitro or ex vivo sample;
the method may be used to monitor the relative amounts of said marker(s) in said subject at two or more different points in time;
the method may be used to monitor any changes in the amount of said marker(s) in said subject in real-time;
the method may further comprise administering a therapeutic agent that treats infection and/or inflammation to a subject that has been identified as having infection or inflammation by a method of the invention;
the sample may be a sample of whole blood, urine, CSF or synovial fluid; and/or
the sample may comprise neutrophils.

The methods of the invention may detect said marker(s) using one or more biosensors, wherein each biosensor comprises (a) a biological element that is capable of recognising said marker(s) and (b) an electrode capable of detecting a reaction caused by the recognition of said marker(s) by the biological element. For example:
detection of glutamate may carried out using a biosensor comprising glutamate oxidase, optionally wherein said glutamate oxidase catalyses a reaction of glutamate in the sample to form 2-oxoglutarate+$NH_3$+$H_2O_2$, and wherein an electrode in said biosensor detects said production of $H_2O_2$;
detection of lactate may be carried out using a biosensor comprising lactate oxidase, optionally wherein said lactate oxidase catalyses a reaction of lactate in the sample to form pyruvate+$H_2O_2$ and wherein an electrode in said biosensor detects said production of $H_2O_2$
detection of ATP may be carried out using a biosensor comprising glycerol kinase and glycerol-3-phosphate oxidase, optionally wherein said glycerol kinase and glycerol-3-phosphate oxidase catalyse a reaction of ATP in the sample to form glycerine phosphate+$H_2O_2$, and wherein an electrode in said biosensor detects said production of $H_2O_2$;
detection of acetylcholine may be carried out using a biosensor comprising acetylcholine esterase and choline oxidase, optionally wherein said acetylcholine esterase and choline oxidase catalyse a reaction of acetylcholine in the sample to form betaine aldehyde+$H_2O_2$, and wherein an electrode in said biosensor detects said production of $H_2O_2$,
detection of D-serine may be carried out using a biosensor comprising D-amino acid oxidase, optionally wherein said D-amino acid oxidase catalyses a reaction of D-serine in the sample to form 2-oxo-3-hydroxypropionate+$NH_3$+$H_2O_2$, and wherein an electrode in said biosensor detects said production of $H_2O_2$; and/or
detection of adenosine is carried out using a biosensor comprising adenosine deaminase, nucleoside phosphorylase and xanthine oxidase, optionally wherein said adenosine deaminase catalyses a reaction of adenosine to form inosine, said nucleoside phosphorylase catalysed a reaction of inosine to form hypoxanthine and said xanthine oxidase catalyses a reaction of said hypoxanthine to form urate and $H_2O_2$, and wherein an electrode in said biosensor detects said production of $H_2O_2$.

The invention also provides a method of preparing an apparatus for measuring the level of at least one marker selected from glutamate, ATP, D-serine, acetylcholine and adenosine in whole blood, the method comprising: (a) providing an apparatus capable of sampling, treating, taking measurements from or manipulating whole blood ex vivo or in vivo; (b) incorporating into said apparatus of (a) a biosensor capable of detecting glutamate, lactate, ATP, D-serine, acetylcholine and adenosine in whole blood, such that said biosensor will be in contact with the whole blood as the blood is contacted with the apparatus. The biosensor may be any biosensor as described herein. The invention also provides an apparatus that is obtainable by such a method. The methods of the invention may be carried out using such an apparatus.

BRIEF DESCRIPTION OF THE FIGURES

FIG. 1 shows experiments using a biosensor to detect glutamate levels.

FIG. 2 shows the effects on ATP levels. FIG. 3 shows the effects on D-serine levels. FIG. 4 shows the effects on acetylcholine levels. FIG. 5 shows the effects on adenosine levels.

FIG. 6 shows glutamate concentration and FIG. 7 shows lactate concentration.

DETAILED DESCRIPTION OF THE INVENTION

Figure 1A:
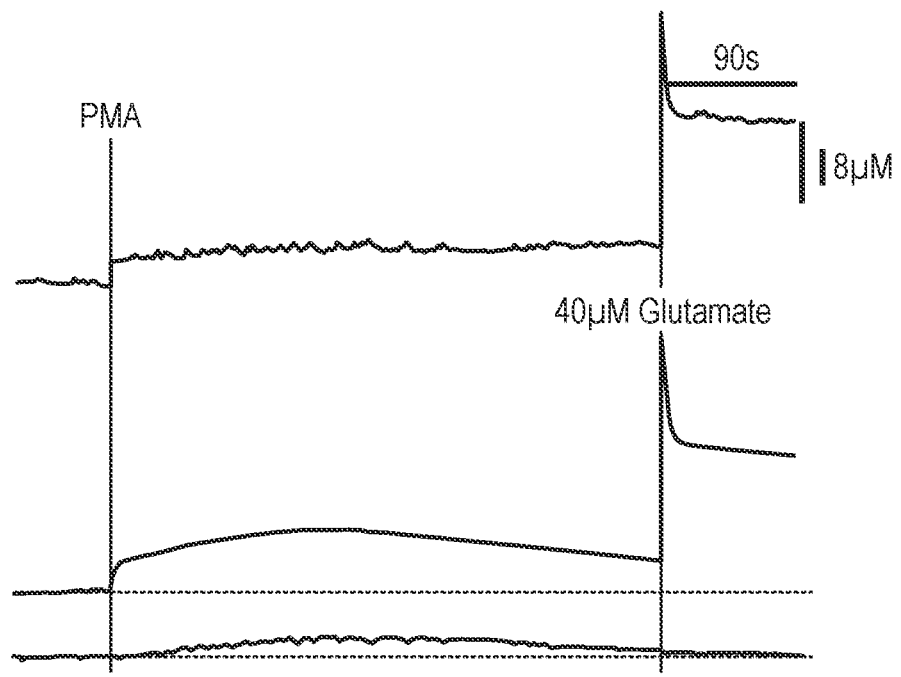
FIG. 1A shows the levels of glutamate after treatment of whole blood with PMA.

The present invention is based on the finding that specific molecules, referred to herein as immunotransmitters, are released upon activation of immune cells. One example of this is the release of glutamate by neutrophils upon stimulation (see FIG. 1). This activation of immune cells, and the release of the immunotransmitters, can be blocked by specific antagonists.

It is possible to identify different patterns of release, and characteristic signatures that are associated with, or diagnostic of, specific immune states. For example, lack of response to a stimulus may be consistent with immunosuppression or may indicate the presence of an existing infection or inflammatory response in the subject. The Inventors have found that the patterns and signatures of release of several molecules change in time- and concentration-dependent patterns.

The present invention therefore relates to methods in which such immunotransmitters are detected or monitored. The detection or monitoring may involve detecting the presence or absence of one or more immunotransmitters. The detection or monitoring may involve the quantification of the amount of one or more immunotransmitters. The detection or monitoring may involve the quantification of the relative amount of one or more immunotransmitters, such as detecting or monitoring any increases or decreases that occur in the amount of said one or more immunotransmitters, over time or in response to a stimulus. The methods of the invention may involve any one, two or all three of these types of detection or monitoring.

The method of the invention may involve determining or monitoring the presence, amount or relative amount of one or more immunotransmitters over a period of time. The method may involve comparing the presence, amount or relative amount of one or more immunotransmitters with the presence, amount or relative amount of said immunotransmitter(s) in a control sample. The method may involve determining whether a stimulus alters the presence, amount or relative amount of one or more immunotransmitters.

Many of the molecules to be detected as described herein are released rapidly and may also be rapidly degraded or may otherwise be rapidly removed from the cells that had produced them. It is therefore advantageous to detect such molecules rapidly. Rapid detection also allows for more accurate determination of any patterns in the presence, amount or relative amount of any immunotransmitters.

Immunotransmitters

In one embodiment, the invention provides markers (also referred to herein as immunotransmitters or target molecules) that can be used to detect or diagnose the presence of inflammation or infection in a patient or subject. In particular, it has been found that glutamate, lactate, ATP, D-serine, acetylcholine and adenosine can each be used as a marker for the presence of inflammation or infection.

As described herein, the marker may be selected from the group consisting of glutamate, lactate, ATP, D-serine, acetylcholine and adenosine. The marker may be any one of these molecules. The methods of the invention may involve detecting any one or more of these markers, such as any one, two, three, four, five or all six of these molecules.

That is, where the methods described herein refer to the detection of a target molecule, marker or marker(s), this is intended to encompass methods in which any one, any two, any three, any four, any five, or all six of these molecules are detected.

Samples for Testing

The methods of the invention involve detecting one or more markers in a biological sample. The sample is typically a sample that has been obtained from a subject of interest. The sample may be any biological sample, preferably a liquid sample.

The sample preferably contains cells, such as immune cells. The sample preferably contains neutrophils. The sample may contain monocytes. The sample may be a sample of whole blood, urine, CSF or synovial fluid. The sample may be a sample of heparinised whole blood. The sample may be a sample of plasma or serum.

The sample may be purified before it is tested accordance with the present invention. For example, the sample may be concentrated or purified to obtain a higher concentration of cells, or a higher concentration of particular types of cells, such as a higher concentration of neutrophils. For example, the sample may comprise immune cells, such as neutrophils. The sample may be a sample of neutrophils. The sample may be obtained by purifying immune cells, such as neutrophils, from a sample obtained from the subject, such as a blood sample. Methods for purifying particular cell types are known in the art. For example, one method for preparing neutrophils from whole blood is described in the Examples below.

Most preferably the sample is a sample of whole blood or a sample of neutrophils.

In some embodiments it is desired to carry out the method of the invention rapidly after the sample has been obtained from the subject. For example, where the method is carried out on a sample of whole blood, it is preferable not to store the blood before testing. In some embodiments, therefore, a method of the invention is carried out on a sample less than 10 minutes, less than 5 minutes or less than 1 minute after the sample has been obtained from the subject.

The subject of interest may be a human or a non-human animal. The term "non-human animal" includes all vertebrates, e.g. mammals and non-mammals, such as non-human primates, sheep, dogs, cats, horses, cows, chickens, amphibians, reptiles, etc. The subject is preferably a human. The subject may be of any age. For example, the subject may be a baby or infant. The subject may be a child or adolescent. The subject may be an adult subject such as an adult human.

Detection Methods

The methods of the invention involve detecting the presence of one or more markers in the sample. Any method capable of detecting the marker(s) may be used.

Preferably, the methods of the invention assess changes or differences in the amount of the marker(s) of interest. The method used is therefore preferably capable of quantifying the amount of the marker(s), or detecting changes in the level of the marker(s). This may be a change in the amount of the marker(s) in a sample when the sample is contacted with a stimulus. Alternatively, this may be a difference in the amount of the marker(s) between two different samples, between a test sample and a control sample or a control value, or between a sample when measured before or after a stimulus.

A method of the invention may involve detecting one or more markers as described herein in a sample from a subject of interest. The amount of said marker(s) may be assessed to determine whether the amount is different to the amount that would be expected in a control sample such as a sample from a normal subject.

As seen in the Examples, stimulation of the immune system can lead to a prolonged increase in the levels of such markers. Such an increase may be detected in a sample from a subject and may indicate that the subject has an infection or inflammation. For example, if the level of said marker(s) is greater than that of a control, such as significantly greater than the level that would be expected in a normal control sample, this may indicate that the subject has infection and/or inflammation.

Any change (increase or decrease) in the level/amount of marker(s) as described herein may indicate the presence of an infection or inflammation in the subject. In particular, an increased level of the marker(s) may indicate that the subject has an infection or inflammation. A change in the level/amount of marker(s) may be assessed by comparing the level/amount of the markers in a sample from the subject with a control value. A control value may be obtained from a sample from a normal subject, such as a sample obtained from a subject that does not have an infection or inflammation. A control value may be obtained from a different sample from the same subject, such as a sample obtained from the subject at a time when it is known that the subject does not have an infection or inflammation.

A control sample is preferably the same sample type as the sample of interest, for example both samples may be samples of whole blood. The comparison with a control may be a direct comparison between the sample or interest and a control sample, i.e. the two samples may be processed in parallel as part of a single experiment. Alternatively, the comparison may be based on an existing control value based on one or more earlier measurements taken from control samples. The control value and/or the value obtained from the sample of interest may be normalised to take account of different sample sizes, or different amounts or concentrations of cells, such as neutrophils, in each sample.

A difference between the level of marker(s) in a subject and the level that would be expected in a control subject or sample may be assessed by comparing the level of the marker(s) in the subject of interest with the level of the same marker(s) in one or more normal or control samples, or with a known level of said marker(s) obtained from previous analysis of samples from normal or control subjects.

If the level of said marker(s) in the sample from the subject of interest is significantly higher or significantly lower than such a control value, this may indicate that the subject has an infection or inflammation.

A significantly higher or lower level may be assessed by routine methods. For example, a level that is lower or greater than the 95% population level of said marker(s) may be considered to be different than the level that would be expected in a normal subject. When a method of the invention finds a level of one or more of said markers which is greater or lower than would be found in 95% of the population, this may indicate that the subject from whom the sample was obtained has an infection or inflammation. For example, if samples from 95% of normal subjects would show a maximum level of marker(s) at a particular amount, a sample of interest may be considered to have a significantly higher level if the amount of said marker(s) in said sample is greater than that 95% value. Such an increased or decreased level of marker(s) may indicate that the subject has an infection or inflammation. A control value may therefore be obtained by measuring the amount of said marker(s) in samples obtained from multiple subjects, such as multiple normal subjects, and obtaining an average, and/or 95% population level of said marker(s) from said sample.

A method of the invention may comprise a step of applying a stimulus to the sample and detecting any change in the level of the marker(s) of interest in the sample. The marker(s) may be molecules, referred to herein as immunotransmitters, that are released upon activation of immune cells in response to such stimulation. This may be carried out as an additional step in any method of the invention as described herein, or this may be carried out as an independent method. For example, the invention provides a method of detecting infection or inflammation in a mammalian subject, the method comprising: (a) applying a stimulus to a sample from a subject, and (b) detecting any change in the amount of at least one marker selected from glutamate, lactate, ATP, D-serine, acetylcholine and adenosine in said sample before and after said stimulus is applied; and optionally (c) comparing any change detected in step (b) with the change in the amount of said marker(s) which is seen when said stimulus is applied to a control sample. In such methods, the control sample may be any control sample or control value as described herein, the sample may be any sample as described herein, the subject may be any subject described herein and the marker(s) may be detected by any suitable method as described herein. In such methods, an increased or decreased response of said marker(s) to the stimulus in the sample from the subject, when compared to the response to the stimulus in the control sample, is indicative of the presence of inflammation or infection.

In some embodiments the invention provides a method of detecting infection or inflammation in a mammalian subject, the method comprising: (a) applying a stimulus to a sample from a subject, and (b) detecting any change in the amount of at least one marker selected from glutamate, lactate, ATP, D-serine, acetylcholine and adenosine in said sample before and after said stimulus is applied; and optionally (c) comparing any change detected in step (b) with a control value for the said change. The control value and/or the value obtained from the sample of interest may be normalised to take account of different sample sizes, or different amounts or concentrations of cells, such as neutrophils, in each sample, or of the amount or concentration of stimulant with which the sample is brought into contact.

An increased or decreased response of said marker(s) to the stimulus applied to the sample from the subject, when compared to the response to the stimulus applied to the control sample, may be indicative of the presence of inflammation or infection. If the change in the amount of said marker(s) in the sample from the subject of interest is significantly higher or lower than a control value, this may indicate that the subject has an infection or inflammation.

A significantly higher or lower change may be assessed by routine methods. For example, a change that is lower or greater than the 95% population change of said marker(s) in response to the said stimulus may be considered to be different from the change that would be expected in a normal subject. When a method of the invention finds a change of one or more of said markers which is greater or lower than would be found in 95% of the population, this may indicate that the subject from whom the sample was obtained has an infection or inflammation. For example, if samples from 95% of normal subjects would show a maximum change of marker(s) at a particular amount, a sample of interest may be considered to have a significantly higher change if the change in the amount of said marker(s) in said sample are greater than that 95% value. Such an increased or decreased change in the amount of marker(s) may indicate that the subject has an infection or inflammation. A control value may therefore be obtained by measuring the change in the amount of said marker(s) in response to the stimulus, in samples obtained from multiple subjects, such as multiple normal subjects, and obtaining an average, and/or 95% population level of said marker(s) from said sample.

In particular, a decreased response, such as a decreased in the change in the amount of said marker(s) in the sample, or a small or negligible change with respect to noise or background signal in the measurement, following contact of the sample with the stimulator may indicate that the subject has an infection or inflammation.

A change that is less than a certain factor of the said control value may indicate that the subject has an infection or inflammation, such as a change that is less than 0.9 times, or 0.8, 0.7, 0.6, 0.5, 0.4, 0.3, 0.25, 0.2, 0.1, 0.05, 0.01, 0.005 or 0.001 times the control value or times a response from the same stimulus applied to a normal control sample.

A control value for the change in marker concentration in response to stimulation may be the change in the said marker concentration in a control sample or an average of the changes in a set of control samples, as described herein.

The sample may be stimulated by contacting it with a stimulator or activator of immune cells. The stimulus may be any stimulator of the immune system or of immune cells. The stimulus may be a stimulator of the type of immune cells that are present in the sample. For example, if the sample is a sample of neutrophils or a sample comprising neutrophils such as a whole blood sample, the stimulus may be a stimulator of neutrophils. Such a stimulus may be a stimulator of neutrophil activity, for example, a stimulator of neutrophil phagocytic activity or a stimulator of neutrophil degranulation.

The stimulus may be a pathogen or may be derived from a pathogen. For example, the stimulus may be a pathogen such as bacterial cells. The pathogen may be inactivated or may be active. The pathogen may be treated to make it more likely to provoke a response from the immune system. For example, the stimulus may be a pathogen or a pathogenic component that has been opsonised. For example, the stimulus may be bacterial cells or opsonised bacterial cells. As illustrated in the Examples, suitable bacterial cells may be $E.$ $coli$. The $E.$ $coli$ may be opsonised $E.$ $coli$.

A stimulus may be a component or molecule that is derived from, or characteristic of, a pathogen. For example, the stimulus may be a pathogenic molecule such as PMA (phorbol myristate acetate) or LPS (lipopolysaccharide), an N-formylated peptide such as fMLP (f-Met-Leu-Phe), monosodium urate or a fungal wall extract. The stimulus may be a component of a pathogen such as a fragment of a pathogen. The stimulus may be a component of a pathogen such as a bacterial cell component.

The stimulus is preferably a stimulus that causes a change in the amount or level of the marker(s) in a control sample such as a sample from a normal subject. As discussed herein, a normal subject may be a subject that does not have inflection or inflammation. For example, a suitable control sample as described herein, such as a sample of blood or neutrophils from a normal subject, may be contacted with a possible stimulus and the amount of the marker(s) of interest assessed in said sample, for example by a detection method as described herein. If the stimulus causes an increase or a decrease in the amount of said marker(s) in said control sample, then this indicates that the stimulus used in said experiment is a suitable stimulus for use in a method as described herein, in which it is intended to determine whether a subject has infection or inflammation.

The methods of the invention may involve detecting the presence of, or the amount of, the marker(s) before and/or during and/or after the application of the stimulus. This may allow the detection of any changes in the presence of or amount of the marker(s) when the stimulus is applied, and any changes in the presence or amount of the marker(s) after the stimulus has been applied.

The release of the marker(s) of the invention may be rapid when the stimulus is applied. It is therefore preferred that the detection method that is used is capable of detecting such rapid changes. Preferably the detection is carried out within 10 minutes, within 5 minutes, within 2 minutes, within 1 minute, within 30 seconds or within 20 seconds of applying the stimulus.

The speed of release of a marker may be different for different markers. As illustrated in the Examples, glutamate release may be seen rapidly after a stimulus is applied. For example, in accordance with the present invention, a method may be used to assess whether an increase in glutamate has occurred within 10 minutes, within 5 minutes, within 1 minute, within 30 seconds, or within 20 seconds of contacting the sample with a stimulus. The same timescales may also be used where the marker is lactate, ATP, acetylcholine or adenosine. Where the marker is D-serine, a method may be used to assess whether an increase in D-serine has occurred within 10 minutes, within 5 minutes or within 2 minutes of contacting the sample with the stimulus. The detection may be carried out in real-time when the stimulus is applied. For example, the amount of the marker(s) may be continuously assessed in the sample. Any changes in the amount of the marker(s) may be monitored before and/or during and/or after the application of the stimulus. For example, as discussed in more detail below, the detection may be carried out using a biosensor such as a biosensor which is capable of detecting the presence or amount of the marker(s), and converting that chemical information into an electrical signal that can be monitored. The method may thus include continuous or real-time monitoring of the presence or amount of the marker(s) in a sample. Where the method uses a biosensor, any effects of a stimulus may thus be detected rapidly and will be seen as changes in the electrical signal that is detected by the biosensor.

It is preferred that the method allows for selective or specific detection of the marker(s) of interest. That is, it is preferred that the method preferentially detects the marker(s) of interest rather than any other molecules in the sample.

It is preferred that the method preferentially detects the amount or levels of the marker(s) or changes in those amounts or levels rather than any other changes in the sample, such as changes in the amount or level of other molecules or changes of other conditions in the sample.

In some methods, one or more markers as defined herein are specifically or selectively detected or measured in the method. A marker is selectively measured if the method detects that marker with greater sensitivity than the detection of other molecules.

For example, the method may involve detecting one or more markers by the binding of said marker(s) to a ligand or other molecule such as an antibody. Where such a ligand or antibody is used to detect a marker(s), the ligand or antibody will preferably bind to the marker(s) of interest with greater binding affinity than that at which it binds to another molecule. The term "binding affinity" is intended to refer to the tendency of a ligand or antibody molecule to bind or react with a target. Binding affinity may be quantified by determining the disassociation constant (Kd) for an antibody or ligand and its target. The specificity of binding of an antibody or ligand to its target may be defined in terms of the comparative dissociation constant (Kd) of the antibody or ligand for its target as compared to the dissociation constant with respect to the antibody or ligand and another, non-target molecule. Typically, the Kd for the antibody or ligand with respect to its target will be two-fold, preferably five-fold, more preferably ten-fold less than the Kd with respect to another, non-target molecule such as an unrelated molecule or accompanying molecule in the same sample. More preferably, the Kd will be fifty-fold less, even more preferably one hundred-fold less, and yet more preferably two hundred-fold less.

The detection method may utilise a reaction that requires the presence of the marker(s) of interest. Where such a method is used, it is preferable that the reaction is selective for the desired marker(s) of interest. That is, it is preferred that the reaction will only take place in the presence of the desired marker(s) and not in the presence of other molecules, such as other related molecules. For example, where the method of detection utilises an enzyme that catalyses a reaction, the enzyme is preferably an enzyme that will react selectively with the marker(s) of interest so that the enzymatic reaction will only take place when the target marker of interest is present.

The detection method may be chosen on the basis that the marker(s) of interest is the only component of the enzymatic reaction, or the only molecule bound by the antibody or ligand, that is expected to be present in the sample, or the only such component or molecule whose levels are expected to vary within the sample. For example, any other component that might take part in the same reaction or molecule that might be bound by the antibody or ligand would be expected to have consistent levels in different samples or during the time period of the measurement, such that any differences or changes in measurements that are observed can be linked to changes in the amounts of the markers of interest.

In those methods where a stimulus is applied, the effect of that stimulus on the marker(s) is assessed. The method may comprise determining whether there is any increase or decrease in the amount of the marker(s) in response to the stimulus. The method may comprise determining whether the response to said stimulus is different to the response that would be expected in a sample from a normal subject.

As seen in the Examples, where a sample has been pre-exposed to a pathogenic stimulus, its response to a later stimulus may be changed. For example, if a subject already has an infection or inflammation, a sample from that subject may be less responsive to a stimulus than a sample from a subject not having infection or inflammation. For example, if the release of marker(s) in response to a stimulus is less, smaller or slower than would be expected based on a control value, such as significantly less, smaller or slower than the release or response that would be expected in a control sample, this may indicate that the subject has already been exposed to a stimulator of immune response. The subject may therefore have infection and/or inflammation.

A different response to a stimulus, such as an increased response or a decreased response to the stimulus, may indicate that the subject already has an infection or inflammation.

A different response to a stimulus may thus indicate that the subject has already been exposed to a pathogen, such as a bacterial, viral or fungal pathogen. It may thus indicate that the subject is already suffering from an infection.

A different response to a stimulus may indicate that the sample had a reduced immune response to the stimulus. For example, a reduced response to the stimulus may indicate that the subject is immunosuppressed. The methods of the invention may therefore be used to identify subjects that are immunosuppressed.

Any difference in the response to stimulus of marker(s) as described herein may indicate the presence of an infection or inflammation in the subject. In particular, if the response to said stimulus is decreased compared to normal (e.g. a control sample or control value), this may indicate that the subject has an infection or inflammation.

A difference in response to a stimulus is a difference between the response to the stimulus in a sample from said subject and the response to the stimulus that would be expected in a sample from a normal subject. This can be assessed by comparing any changes in the levels of said marker(s) in response to said stimulus in a sample from a subject and any changes in the levels of said marker(s) in response to said stimulus that would be expected in a control sample such as a sample from a normal subject. For example, where a stimulus causes a change in the level of said marker(s) in a sample from a normal subject, the size, time of onset or duration of that change in level may be assessed. Any difference in the size, time or duration of a response to stimulus in a sample from the subject of interest compared to the response that would be expected in a sample from a normal subject may indicate that the subject of interest has an infection or inflammation.

A difference in response to a stimulus may be expressed as a difference in the response following contact of the sample with a stimulator of immune cells from a control value for the said difference, the control value being the response that would be expected in a control sample such as a sample from a normal subject. Such a control value may be derived from one or more tests on such control samples from normal subjects, and a control value may be an average of the responses from a number of such tests. A control value may lie in a range, such as a range of values expected from tests on a number of control samples.

A control value or a said range may be derived for a chosen subject subpopulation, such as a population having one or more defining characteristics, such as age, sex or presence of a further health condition. In this way in a method of the invention a control value or range within which a control value may lie may be selected that is suitable for the subpopulation of which a subject is a member. For example, immunosuppression may be known to be present in a certain subpopulation, and a lower control value may be used in the method for a patient from this subpopulation than for a patient from a different subpopulation.

For example, as shown in the Examples, the amount of a marker that is released in response to a stimulus can be assessed by calibrating the amount of marker. Known amounts of the marker can be added to a sample and the increase that is seen as a result of that addition can be compared with the change that was seen in response to the stimulus. The amount of the marker that is released in response to a stimulus can therefore be determined.

If the amount of the marker(s) after a stimulus is different (increased or decreased) in a sample from a subject of interest when compared to the amount of said marker(s) after stimulus that would be expected in a control sample, e.g. from a normal subject, this indicates that the subject of interest may have an inflection or inflammation. For example, if the amount of said marker(s) after stimulus is less than would be expected based on a control, this may indicate that the subject of interest has an infection or inflammation.

As shown in the Examples, a stimulus may cause an change, such as an increase, in the amount of a marker, even in a sample that is representative of an infected subject. However, the amount or size of that change may be different to that expected in a normal sample. For example, the amount of marker(s) may increase in response to stimulus, but may increase by less than would be expected in a normal sample. This would be a difference in response as described herein that may indicate that the subject of interest has an infection or inflammation.

Similarly, the timing of a response to stimulus can be assessed. The same comparisons discussed above in relation to the amount of a marker may apply to the timing of any changes in the marker(s). For example, any change in marker(s) in response to stimulus may occur more quickly, more slowly, or with longer or shorter duration, in a sample from a subject having an infection or inflammation than in a sample from a normal subject.

The response to a stimulus that would be expected in a normal subject may be determined by carrying out the method of the invention on a sample of interest and also carrying out the same method on a control sample from a known normal subject. This may allow a direct comparison of the response to stimulus from the two samples. The response to stimulus in a sample from a subject of interest may be compared with the response to stimulus in samples from one or more normal subjects, or with a known response to stimulus of said marker(s) obtained from previous analysis of samples from normal subjects. For example, a control value may be obtained by assessing the change in amount of said marker(s), or the timing of any changes in amount of said marker(s), in a population of subjects that do not have an infection or inflammation. As described herein, a normal subject is a subject that does not have an infection or inflammation. A control sample or control value may be any control sample or value as described herein. The control sample may be the same control sample discussed above in relation to the level of the marker(s) in the absence of a stimulus.

If the response to stimulus of said marker(s) in the subject of interest is significantly different to such a control response, this may indicate that the subject has an infection or inflammation. A significant difference may be assessed by routine methods. For example, a control value can be obtained by determining the response to the stimulus for 95% of the population, or 95% of non-infected and non-inflammatory subjects. The response of a subject of interest can then be compared to that 95% value. A response that is different to the 95% population level may be considered to be different than the response that would be expected in a normal subject. Where a method of the invention finds a response which is different to the response that would be found in 95% of the population, this may indicate that the subject from whom the sample was obtained has an infection or inflammation. For example, if samples from 95% of normal subjects would show an increase of marker(s) of at least a particular amount or in a particular timescale or duration, a sample of interest may be considered to have a different response if the increase of said marker(s) in said sample is less than that 95% value. Such a reduced response to the stimulus may indicate that the subject has an infection or inflammation, or that the subject is immunosuppressed.

Where a method of the invention assesses the amount or level of marker(s), these may be compared with a control value in order to determine whether the amount or level is increased or decreased. A control value may be obtained by measuring the amount or level of the same marker(s) in a control sample. A suitable control sample may be, for example, a sample from a subject that is known to have no infection or inflammation. A suitable control may therefore be a normal sample. A suitable control may be such a normal sample which is of the same sample type as the sample being tested, e.g. a sample of whole blood. A normal sample may be processed in parallel with the sample being tested to allow a direct comparison between the two samples. Alternatively, the test sample may be compared with known control values, such as values or responses obtained previously by assessing a normal control sample under suitable control conditions.

A suitable control sample may be such a normal sample that has been processed and treated in the same way as the sample of interest. For example, in the methods described herein where a stimulus is applied to the sample, a suitable control for comparison may be a normal sample under control conditions, i.e. in the absence of a stimulus, a normal sample that has been exposed to the same stimulus as the test sample, or the test sample itself before the stimulus has been applied. The response of the test sample to the stimulus may be compared to any of these controls in order to determine whether there is any change in the amount or level of the marker(s) in response to the stimulus, or whether the change in the amount or level of the marker(s) in response to the stimulus is different to the change that is seen in a normal sample.

Such comparisons with controls can be used to identify any differences in the amounts or levels of the marker(s) in the test sample or any differences in the responses of the test sample to the stimulus.

A control value may be selected in the following ranges to be used in the methods of the invention with a sample as described in the Examples herein, comprising for example whole blood from a human subject, such as undiluted human whole blood, in which the stimulant is PMA added to the sample to have a concentration of 100 nM, or a sample comprising neutrophils derived from human blood at a concentration of 5 million cell s/ml.

A control value for a change in the amount of a marker selected from glutamate, lactate, ATP, D-serine, acetylcholine and adenosine in said sample when the said stimulus is applied may be in the range around 0.5 µM to around 50 µM, such as in the range 0.5 µM to 2 µM, 1 µM to 5 µM, 2 µM to 10 µM, 5 µM to 20 µM, 10 µM to 30 µM, or 20 µM to 50 µM.

A marker may be glutamate and a control value for the change in the amount of glutamate in the said sample may be in the range around 0.5 µM to around 50 µM, such as in the range 0.5 µM to 2 µM, 1 µM to 5 µM, 2 µM to 10 µM, 5 µM to 20 µM, 10 µM to 30 µM, or 20 µM to 50 µM.

A marker may be lactate and a control value for the change in the amount of glutamate in the said sample may be in the range around 1 µM to around 6 µM, such as in the range 1 µM to 3 µM, 2 µM to 4 µM or 3 µM to 6 µM.

A marker may be ATP and a control value for the change in the amount of glutamate in the said sample may be in the range around 0.5 µM to 10 µM, such as around 0.5 µM to 2 µM, 1 µM to 5 µM, or 2 µM to 10 µM.

A marker may be D-serine and a control value for the change in the amount of glutamate in the said sample may be in the range around 0.5 µM to 5 µM, such as 0.5 µM to 2 µM, or 1 µM to 5 µM.

A marker may be acetylcholine and a control value for the change in the amount of glutamate in the said sample may be in the range around 0.5 µM to 5 µM, such as 0.5 µM to 2 µM, or 1 µM to 5 µM.

A marker may be adenosine and a control value for the change in the amount of glutamate in the said sample may be in the range around 0.5 µM to 20 µM, such as 0.5 µM to 2 µM, 1 µM to 5 µM, 2 µM to 10 µM or 5 µM to 20 µM.

It will be understood that the control value may be selected according to the concentration of the sample, and in particular according to the expected concentration of neutrophils in the sample. For example, if human whole blood at 50% dilution, or a neutrophil suspension at 2.5 million cells/ml, were to be tested, control values may be selected in a range 50% of the ranges above.

When the sample is stimulated according to the invention, detection of inflammation or infection may occur when there is a difference in the response to stimulus between the sample being tested and a control sample as defined herein. Typically, the response in the sample being tested will be higher or lower than the response in the control sample, for example at least 10-fold at least 5-fold, at least 2-fold or at least 1.5-fold higher or lower. In the case of glutamate as a marker, the response of the sample being tested may for example be at least 1.5-fold, at least 2-fold, at least 2.5-fold, or at least 3-fold lower than that in a sample from a healthy control. In the case of lactate as a marker, the response of the sample being tested may for example be at least 2-fold, at least 3-fold or at least 5-fold lower than that in a sample from a healthy control.

Biosensors

In one embodiment, the marker(s) of interest is detected using a biosensor. A biosensor is an electrode that comprises a biological element that is capable of recognising the marker(s) of interest. This biological element may be or may comprise a biorecognition molecule such as an enzyme, antibody, organelle or whole cell. A suitable electrode may therefore comprise an enzyme, antibody, organelle or whole cell which is capable of recognising the marker(s) of interest. The biological element may be specific for or selective for the marker(s) of interest. Preferably, the biological element is capable of recognising a marker selected from glutamate, lactate, ATP, D-serine, acetylcholine and adenosine.

The biological element may be a biological molecule, cell or cell part that is capable of detecting the presence of the marker(s) of interest. For example, the biological element may be a molecule that selectively or specifically binds to the marker(s) of interest, i.e. a biorecognition molecule.

Such a biological element may be, for example, an antibody, aptamer, receptor or ligand that is capable of binding to or otherwise detecting the presence of the marker(s) of interest. A suitable antibody may be a whole antibodies or an antibody fragment, such as IgG, IgM or Fab or a single chain antibody. A suitable antibody will be capable of binding to the marker(s).

The biological element may be an enzyme, such an enzyme for which the marker(s) of interest is a substrate. For example, the enzyme may be selected from one or more of xanthine oxidase, glucose oxidase, lactate oxidase, cholesterol oxidase, galactose oxidase, glutamate oxidase, horseradish peroxidase, polyphenol oxidase, D-fructose dehydrogenase, L-glutamate dehydrogenase, alcohol dehydrogenase (such as methanol dehydrogenase), urease, uricase, lactate dehydrogenase, glutamic pyruvic transaminase, creatinase, sarcosine oxidase, glutaminase, nucleoside phosphorylase, ascorbate oxidase, cytochrome C oxidase, adenosine deaminase, D- or L-amino acid oxidase, tyrosinase, catalase, phosphoenolpyruvate kinase, glycerol kinase, glycerol-3-phosphate oxidase, phosphocreatine kinase, acetylcholine esterase, choline oxidase and/or choline dehydrogenase. Other enzymes known in the art may also be used.

Typically, the biological element, such as one or more enzymes, detects the presence of the marker(s) of interest and acts to provide an electroactive substance for detection by the transducer. The biological element may produce a diffusible molecule, such as $H_2O_2$ which is detected at the electrode. Alternatively, a mediator may be used to transfer electrons to or from the electrode of the biosensor.

For example, the biological element may comprise one or more enzymes, where the enzyme(s) use the marker(s) of interest as a substrate, and wherein in the presence of that marker(s), the enzyme(s) catalyse a reaction that results in the production of $H_2O_2$. The presence of such $H_2O_2$ may be detected by the electrode. For example, the electrode may electrochemically oxidise the $H_2O_2$ to produce an amperometric signal.

Where the marker is glutamate, the biological element may comprise glutamate oxidase. The biological element may catalyse a reaction of glutamate in the sample to form 2-oxoglutarate+$NH_3$+$H_2O_2$.

Where the marker is lactate, the biological element may comprise lactate oxidase. The biological element may catalyse a reaction of lactate in the sample to form pyruvate and $H_2O_2$.

Where the marker is ATP, the biological element may comprise glycerol kinase and glycerol-3-phosphate oxidase. The biological element may catalyse a reaction of ATP and glycerol to form ADP and glycerol-3-phosphate, and a reaction of that glycerol-3-phosphate to form glycerine phosphate and $H_2O_2$. Enzymatic amplification can be achieved by further including creatine kinase.

Where the marker is acetylcholine, the biological element may comprise acetylcholine esterase and choline oxidase. The biological element may catalyse a reaction of acetylcholine in the sample to form choline and acetate and a further reaction of that choline to form betaine aldehyde and $H_2O_2$.

Where the marker is D-serine, the biological element may comprise D-amino acid oxidase. The biological element may catalyse a reaction of D-serine in the sample to form 2-oxo-3-hydroxypropionate+$NH_3$+$H_2O_2$.

Where the marker is adenosine, the biological element may comprise adenosine deaminase, nucleoside phosphorylase and xanthine oxidase. The biological element may catalyse a reaction of adenosine in the sample to form inosine, a further reaction of that inosine to form hypoxanthine and a further reaction of that hypoxanthine to form urate and $H_2O_2$. Such a biological element may also detect inosine and hypoxanthine in the sample, but if desired, it can be used in combination with a further biosensor in which the biological element comprises nucleoside phosphorylase and xanthine oxidase. This would detect inosine and hypoxanthine using the same reaction used in the adenosine sensor and can therefore be used as a control to ensure that only changes in adenosine are detected.

The biological element may comprise two or more biorecognition molecules, such as two or more enzymes. The biological element may comprise two or more biorecognition molecules that are capable of detecting a single marker of interest or two or more biorecognition molecules that are capable of detecting two or more markers of interest. Most preferably, one or more enzymes is used. The ability to induce several enzymes at the same time improves the speed of production of the biosensor and the response obtainable by such biosensors.

The biological element may comprise multiple molecules that act as part of a cascade to detect the marker(s). For example, two or more enzymes may be used together in the form of a cascade to measure one or more different substrates. Typically, such electrodes use an oxidoreductase which is capable of transferring an electron, preferably via a mediator, onto the electrode. Alternatively, the enzyme may be capable of receiving an electron from the electrode, optionally via a suitable mediator.

The biosensor may detect one, two or more markers of interest. The biosensor may comprise one or more biorecognition molecules capable of detecting each such marker.

The biological element is typically attached to a transducer, such as an electrochemical, piezoelectric, optoelectronic, fibreoptic, thermistor, diode or surface acoustic device. The purpose of the transducer is to allow the detection of the binding of the biological element to the marker(s) of interest or the detection of a reaction involving the marker(s) and the biological element. In particular, where the biological element causes the production of an electroactive substance (e.g. $H_2O_2$), the transducer detects that substance and produces a measurable signal. The biosensor may employ a potentiometric, amperometric or impedimetric transducer to convert chemical information into a measurable amperometric signal (Pohanka, J. Appl. Biomed 2008 6:57-64).

Where the method of the invention uses a biosensor to detect or measure one or more markers, the method may also comprise using a control or null sensor. Such a sensor may be a sensor that measures the background level of the substances that are detected by the transducer in the biosensor. For example, where the biosensor uses the production of an electroactive substance (e.g. $H_2O_2$) to transduce a biological signal into an amperometric signal, a null sensor may be used as a control to monitor the levels of such electroactive substances. This can be used to ensure that any changes that are recorded using the biosensor derive from changes in the levels of the marker(s) being detected, and not changes in the levels of such electroactive substances in the sample.

The biological element may be applied to the electrode or other transducer by any suitable means. A variety of methods are known in the art, for example as described by Vasylieva & Marinesco ("Microelectrode Biosensors" Neuromethods, Volume 80, June 2013, pages 95-114, Chapter 5: "Enzyme Immobilization on Microelectrode Biosensors").

For example, one approach involves the use of sol-gel films on substrates, as described in WO 2004/048603. That is, a layer of the biological element may be deposited onto the transducer, such as the electrode, by the selective electrodeposition of a sol-gel at the transducer surface. As explained in WO 2004/048603, this can be achieved for biological molecules by neutralising the acidified sol suspension, prior to applying an electrical current to the electrode. The present invention may therefore use a biosensor which is an electrode or other transducer, onto which a layer of the biological element has been added by a sol-gel method as described on WO 2004/048603.

Further layers may be applied to the electrode or other transducer, for example layers that increase the sensitivity of detection or reduce interference such as interference caused by electroactive species in the test sample. For example, as described in WO 2008/081193 and in Tian et al (Anal Chem 2007 79: 6760-6766), Ruthenium Purple, an analog of Prussian Blue, has advantageous electrochemical characteristics, such as high selectivity against interference by 5HT, ascorbic acid, urate and acetaminophen, high sensitivity with a wide linear calibration range, and good stability. Where the biosensor uses $H_2O_2$ as a product of the biological element, the presence of Ruthenium Purple can reduce the interference caused by electrochemical oxidisation of other molecules and increase the specificity of detection of the $H_2O_2$. The present invention may therefore use a biosensor that comprises Ruthenium Purple, such as a biosensor that comprises a layer of Ruthenium Purple. For example, Ruthenium Purple may be electrodeposited onto the surface of an electrode. The biological element as discussed above may be applied on top of the ruthenium purple, for example forming a layer comprising Ruthenium Purple and a layer comprising the biological element.

Suitable biosensors include probes obtainable from Sarissa Biomedical Limited (Coventry, UK). These include Sarissaprobes® and Sarissagold®. Thus, the biosensor may be a microelectrode having a rigid insulating body with a pin at one end for connection with a potentiostat and a fine sensing tip at the opposite end. The biosensor may comprise a metal wire such as a platinum or gold wire, forming the basis of the electrode. This wire may act as the transducer in the biosensor. Sarissaprobes® use a platinum wire and Sarissagold® use a gold wire. The tip of the wire may be used for detection. That tip may be coated with a biological element as discussed above. The tip may also be coated with other layers, such as additional layers as discussed above to improve sensitivity and reduce interference.

The detection area of the biosensor, such as the tip of the wire as discussed above, may provide a defined sensing area which is contacted with the sample in a method of the invention. The biosensor may be an electrode. The biosensor may be a microelectrode. The detection area may be less than 10 mm long, such as less than 5 mm long, such as 0.5 to 2 mm long. The detection area may any have any of these lengths in combination with a diameter of 5 to 250 µm, such as 5-50 µm such 5 to 10 µm, 5 to 25 µm, 10 to 50 µm or 10 to 25 µm. A typical diameter may be about 7 µm, about 25 µm or about 50 µm.

Both Sarissaprobe® and Sarissagold® sensors detect an amperometric signal proportional to the analyte of interest, depending on the $H_2O_2$ produced within the enzymatic layer. Sarissaprobe® sensors provide a positive amperometric signal due to the oxidation of $H_2O_2$ on the platinum wire, while the Sarissagold® sensors provide a negative signal as the $H_2O_2$ is reduced at the operating potential of −50 mV.

A biosensor as described herein may be used as part of an assay device. For example, a biosensor as described herein may be used in combination with a potentiometer to detect electrical output from the sensor.

A biosensor as described herein may be incorporated into an apparatus to allow the biosensor to be used in a method of the present invention. The apparatus may be an existing apparatus or device that is capable of sampling, treating, taking measurements from or manipulating a biological sample. The apparatus may be configured such that a biological sample as described herein is inserted into, passes through, or comes into contact with the apparatus or a part of the apparatus. For example, the apparatus may be configured or adapted such that a sample of whole blood comes into contact with the apparatus or a part of the apparatus. Such contact may take place in vivo or ex vivo. A biological sample as described herein, such as a sample of blood, may pass through the apparatus before being returned to the subject. Any apparatus that is configured to allow contact of at least part of the apparatus with a suitable sample as described herein may be further adapted by incorporating a biosensor as described herein.

For example, the present invention provides a method of preparing an apparatus for measuring the level of at least one marker selected from glutamate, lactate, ATP, acetylcholine and D-serine and adenosine in whole blood, the method comprising: (a) providing an apparatus capable of sampling, treating, taking measurements from or manipulating whole blood ex vivo or in vivo; and (b) incorporating into said apparatus of (a) a biosensor capable of detecting one or more of glutamate, lactate, ATP, acetylcholine, D-serine and adenosine in whole blood, such that said biosensor will be in contact with the whole blood as the blood is contacted with the apparatus.

The biosensor used in such a method may be any biosensor as described herein.

The invention also provides an apparatus that is obtainable by such a method. The invention provides an apparatus that is capable of sampling, treating, taking measurements from or manipulating whole blood ex vivo or in vivo; wherein the apparatus comprises a biosensor as described herein, such as a biosensor capable of detecting one or more of glutamate, lactate, ATP, acetylcholine, D-serine and adenosine in a sample of blood.

The apparatus may be an existing apparatus or device which is intended to carry out measurements on a biological sample such as a blood sample. For example, a biosensor as described herein may be incorporated into an apparatus intended to carry out measurements on a biological sample. A suitable apparatus may be, for example, a blood dialysis machine, a blood gas monitor or an indwelling catheter which may be for implantation in an artery, vein or body cavity. An apparatus as described herein may be used to carry out a method of the invention. That is, a method of the invention may be carried out using an apparatus as described herein.

Methods of Diagnosis

The invention provides methods of diagnosis that may be used to determine the condition of a subject.

The methods of the invention may be used to detect or diagnose the presence of an infection or inflammation in a subject. For example, the methods described herein may be used to detect or diagnose an infection. The infection may be a pathogenic infection such as a bacterial infection, a viral infection, a fungal infection or a parasitic infection. The infection may comprise sepsis. That is, the methods of the invention may be used to detect or diagnose sepsis in a subject. The infection may comprise bacteremia. The methods of the invention may be used to detect or diagnose inflammation in a subject. For example, the methods may be used to detect or diagnose an inflammatory response or an inflammatory disease in the subject.

Accordingly, the present invention provides a method of detecting infection or inflammation in a mammalian subject, the method comprising: (a) detecting the amount of at least one marker selected from glutamate, lactate, ATP, acetylcholine, adenosine and D-serine in a sample from said subject and (b) comparing the amount of the marker(s) of (a) with the amount of the same marker(s) in a control sample; wherein an increased or decreased amount of said marker in the sample from the subject, when compared to the control value, is indicative of the presence of inflammation or infection.

Preferably, the sample is an in vitro sample.

The diagnostic methods of the invention may comprise any one or more of the steps described herein. For example, the methods may comprise assessing the amount of one or more marker(s) of the invention in a sample and comparing that amount to a control value. The methods may additionally or alternatively comprise stimulating the sample and assessing the response of said marker(s) in the sample to the stimulus.

The diagnostic methods may be carried out using any of the methods described herein, such as using one or more biosensors that detect the marker(s) of interest.

These methods may be used to provide information to a physician in relation to the prognosis and future treatment of a subject. For example, a subject that has been diagnosed with infection or inflammation using a method of the invention may then be treated for said inflammation or infection as a result of that diagnosis. Methods of the invention may further comprise a step administering a therapeutic agent that treats infection and/or inflammation to a subject that has been identified by a method as described herein as having infection or inflammation.

EXAMPLES

Example 1

Materials and Instrumentation

Calibrations were done using L-Glutamic acid, <<insert for lactate>> D-serine, Adenosine and ATP (all Sigma-Aldrich). The buffer used as a common supporting electrolyte was Phosphate Buffered Saline (PBS, pH 7.4, 0.1M) prepared fresh from stock and used for all dilutions made.

Recordings were carried out in a custom made chamber (1.7 ml maximum volume) and the temperature of the chamber was controlled by a Circulator C-85-D. The sensors were connected to a Due-Stat ME200+ potentiostat (Sycopel International Ltd, Jarrow, UK) which was then connected to a Power 1401 interface for processing of the signal. The operating potential for Sarissaprobes was +600 mV and −50 mV for Sarissagold sensors (switched to +600 mV when not operating). The recordings were analysed by Spike2 software.

Preparation of Whole Blood and Human Neutrophils

Blood was collected from patients or from healthy volunteers and stored in heparinised vials (local ethics approved). The samples were kept on ice and were tested within 1 h of collection. This was for experimental convenience: the samples can easily be processed immediately after venipuncture.

Neutrophil preparation from 15 ml of whole blood was achieved by first adding 30 ml PBS under sterile conditions. Half of the PBS/Blood mix was carefully layered on a 15 ml layer of Ficoll-Paque Plus solution in two separate 50 ml falcons using an electronic pipette. The sample was then centrifuged at 1400 rpm at room temp for 30 minutes. 15 ml of sterile blood lysis buffer was added to the pellet centrifuged at 1200 rpm, undergoing 2 lysis cycles. The remaining pellet was washed with sterile PBS, resuspended in 10 ml PBS and the cells were counted. 10 mmol/L of glucose (plasma concentration) was then added in the sample. Neutrophil concentration was adjusted to 5 million cells per ml and stored on ice until the experiment was carried out.

Microelectrode Biosensors

Sarissaprobes and Sarissagold biosensors were used (Sarissa Biomedica, (Coventry, UK). The design and operation of the Sarissaprobe biosensors are described in detail elsewhere (Llaudet et al 2003; 2005, Tian et al, 2009). The Sarissaprobes were used for isolated cells recordings while the Sarissagold biosensors were used for blood recordings. These microelectrodes consist of a rigid insulating body with a pin at one end for connection with the potentiostat and a fine sensing tip on the opposite end. The Platinum (Pt) wire in Sarissaprobes and the gold wire in Sarissagold sensors provide a defined sensing area (50 µm diameter, 1 mm length for Sarissagold sensors and 0.5 mm length for Sarissaprobe sensors) and it is coated with a specialized biorecognition layer, with specific enzymes entrapped, detecting the appropriate analyte of interest and providing a measurable amperometric signal (Pohanka et al, 2008).

Electrochemical biosensors can respond to the analyte of interest as well as other electroactive species present in the samples tested (Murphy et al, 1994). The Sarissaprobe sensors used for these experiments had an internal permselective layer of polyphenylenediamine, greatly increasing their sensitivity and decreasing interference of electroactive species (Masse et al, 2007; Frenguelli et al, 2007; Gourine et al, 2008). Sarissagold biosensors are second generation sensors based on a mediator coated gold electrode. The use of Ruthenium Purple mediator in these biosensors is to reduce the operating potential (decrease the H2O2 detection potential) giving a greater specificity and increased sensitivity in physiological fluid samples such as blood (Tian et al, 2007).

In every experiment a "null" sensor was included, lacking enzymes but otherwise identical, to measure background signals which were then subtracted from the signals generated by the specific operating biosensor, giving a "net" response (Heinrich et al, 2012).

The ATP sensors comprised two enzymes, glycerol kinase and glycerol-3-phosphate Oxidase, the adenosine sensor comprised of three enzymes, adenosine deaminase, nucleoside phosphorylase, and xanthine oxidase while the glutamate sensor contained glutamate oxidase. The D-Serine sensor contained D-amino acid oxidase. The ATP sensor had to be stored in 1M glycerol solution for 30 min to be able to operate.

Both Sarissaprobe and Sarissagold sensors detect an amperometric signal proportional to the analyte of interest, depending on the $H_2O_2$ produced within the enzymatic layer. Sarissaprobe sensors provide a positive amperometric signal due to the oxidation of $H_2O_2$ on the platinum wire, while the Sarissagold sensors provide a negative signal as the $H_2O_2$ is reduced at the operating potential of −50 mV. For comparison, all "net" signals were presented as positive traces.

All sensors were operating against a reference electrode (Ag/AgCl), in a chamber at a stable temperature of 37° C.

The sensors were calibrated after every run with stock solutions: 20 µM (in neutrophils) or 40 µM (in blood) of glutamate, <<insert for lactate>> 1 µM (in neutrophils) or 10 µM (in blood) of D-Serine, 10 µM (in neutrophils) or (13.3 µM) of ATP and 0.748 µM adenosine in blood only. To convert changes in the sensor current to changes in the analyte concentrations, the midpoint of the calibration signal at the end of each run and the midpoint of the peak of the net responses (measured from the extrapolated baseline) were used. This conversion of current to concentration units reduces the limitation of differences in the sensitivity between the biosensors (Gourine et al, 2008).

Experimental protocol 1.5 ml of the prepared sample (whole blood or isolated neutrophils in PBS/glucose) was pipetted into the temperature controlled chamber with a micro-magnetic stirrer for 5 minutes before the sensors were inserted. The sensors were held on a stereotaxic micro-manipulator with the entire sensing tip inserted in the sample, ensuring maximum analyte detection probability. Recordings were done with either all sensors simultaneously or with various combinations according to the sensor availability and aim of the experiment. Once a steady-state baseline was achieved, 100 nM of PMA or opsonised *E. coli* were added to the chamber, avoiding contact with the sensors to limit the noise interference. After any detected response signal levelled off, the calibrations were carried out. A control run was always carried out for each experiment where only PMA/*E. coli* was applied followed by a calibration. The chamber and the sensors were rinsed with PBS or distilled water before every run.

Experiments using Glutamate Sensor

Unless stated otherwise, samples of whole blood from human patients were analysed using the Sarissaprobes and Sarissagold glutamate sensors. In a first experiment, illustrated in FIG. 1A, PMA—which directly stimulates phagocytes—was added to 1 ml heparinised whole blood maintained at 37° C. (as indicated by PMA in FIG. 1A). A null sensor was also used to measure non-specific release of oxygen reactive species. The glutamate sensor detects glutamate release in real time. The tips of the sensors were 2 mm under the surface of the blood during the experiment. Glutamate was added to the chamber at end of experiment (indicated as 40 µM Glutamate in FIG. 1A) to calibrate the concentration of glutamate release.

As can be seen from FIG. 1A, the addition of PMA led to an increase in the response recorded using the glutamate sensor.

Figure 1B:
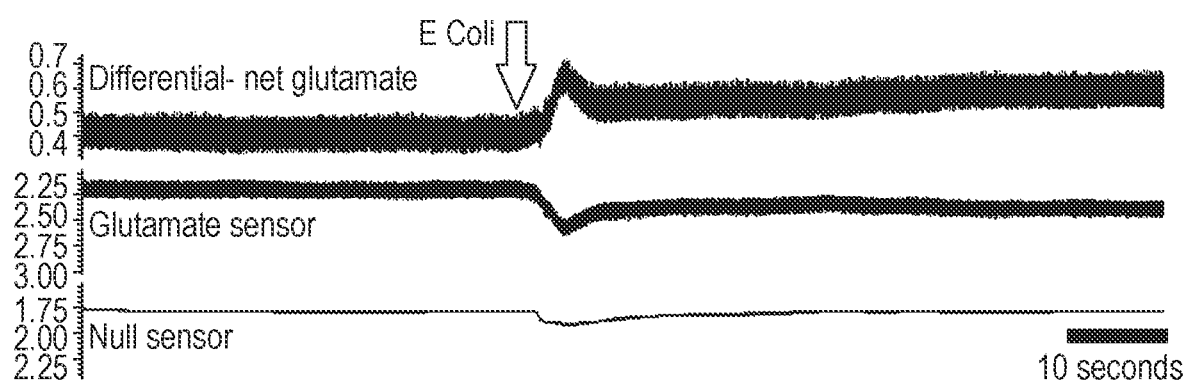
FIG. 1B shows the levels of glutamate after treatment of whole blood with opsonised *E. coli*.

In a second experiment, illustrated in FIG. 1B, opsonised *E. coli* were added to 1 ml heparinised whole blood maintained at 37° C. (as indicated by arrow in FIG. 1B). A null sensor was also used to measure non-specific release of oxygen reactive species. The glutamate sensor detects glutamate release in real time, and the tips of the sensors were 2 mm under the surface of the blood during the experiment.

As can be seen from FIG. 1B, the addition of opsonised E. coli to the blood led to an increase in the response recorded using the glutamate sensor.

Figure 1C:
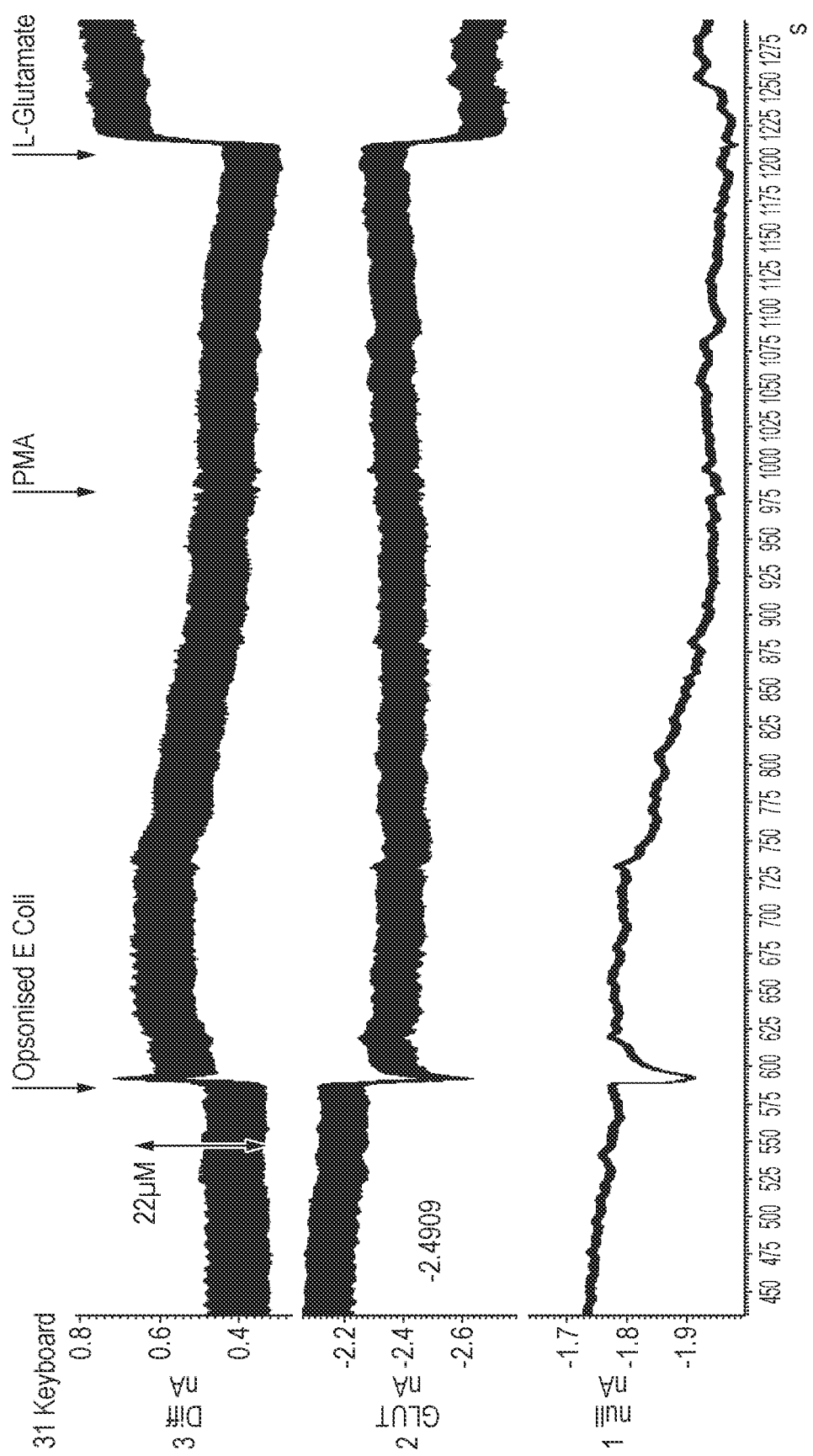
FIG. 1C shows the effect of pretreating whole blood with opsonised *E. coli* before treating with PMA.

In a third experiment, illustrated in FIG. 1C, a combination of different treatments was applied to a sample. Opsonised E. coli was first added to 1 ml heparinised whole blood (indicated as "Opsonised E Coli" in FIG. 1C) to simulate acute bacterial sepsis. Release of 22 µm glutamate was observed. This is consistent with the effect seen in FIG. 1B.

PMA was added subsequently—5 minutes later (as shown in FIG. 1C). PMA failed to increase glutamate release in this experiment. This can be contrasted to the effect seen in FIG. 1A. This indicates a loss of immune response to further stimulation in the sample that had already been treated with the opsonised E. coli. This mimics the situation in a patient already suffering from infection, such as a patient having bacterial sepsis. In a patient that already has infection or inflammation, the response to a subsequent stimulus is reduced. The effect seen in FIG. 1C mimics immunosuppression.

As with the earlier experiments, a null sensor measured non-specific release of oxygen reactive species, the glutamate sensor detects glutamate release in real time, and the tips of the sensors were 2 mm under the surface of the blood. Glutamate was added to chamber at end of experiment (as indicated in FIG. 1C) to calibrate the concentration of glutamate release.

Figure 1D:
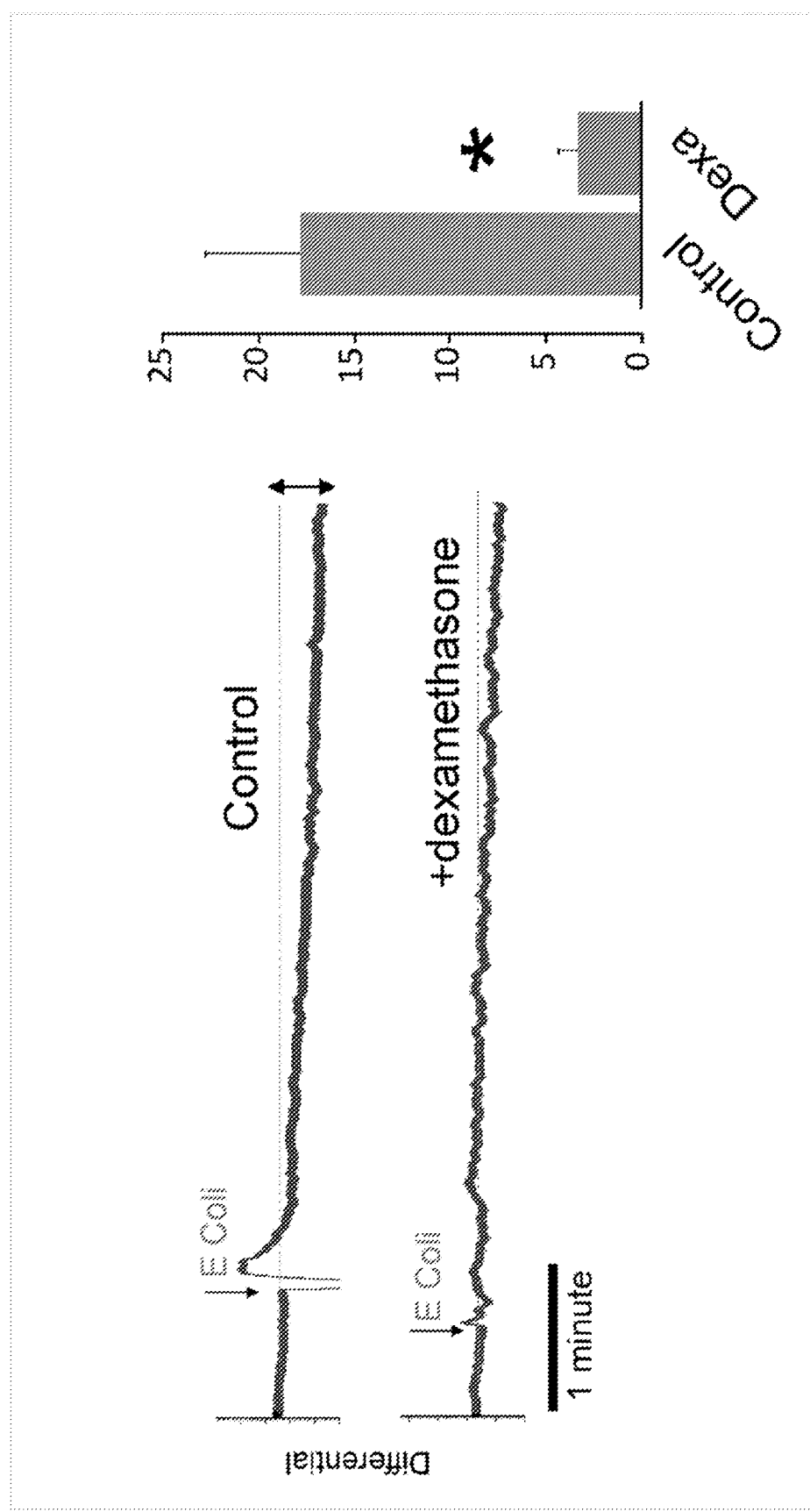
FIG. 1D shows the effects of the immunosuppressant dexamethasone.

In a fourth experiment, as illustrated in FIG. 1D, the effect of the immunosuppressant dexamethasone was assessed. Opsonised E. coli was added to 1 ml heparinised whole blood to simulate acute bacterial sepsis. This is shown on the upper trace in FIG. 1D. A separate sample of 1 ml blood from the same patient was incubated with a therapeutic plasma concentration of the proven immunosuppressant dexamethasone 5 minutes before addition of E. coli (see lower trace in FIG. 1D). The dexamethasone reduced glutamate release under this circumstance, indicating a loss of immune response to further stimulation (mimicking immunosuppression). As in FIG. 1C, if the immune components within the sample are already suppressed, either by dexamethasone or by an existing reaction to an immune stimulus, the subsequent reaction to a stimulus is reduced.

As with the earlier experiments, a null sensor measured non-specific release of oxygen reactive species, the glutamate sensor detects glutamate release in real time, and the tips of the sensors were 2 mm under the surface of the blood. The graph in FIG. 1D shows population data for 5 individuals' blood tested in this way, indicating that the sensors can detect the effect of immunosuppressive doses of dexamethasone on acute bacterial stimulation of whole blood.

Figure 1E:
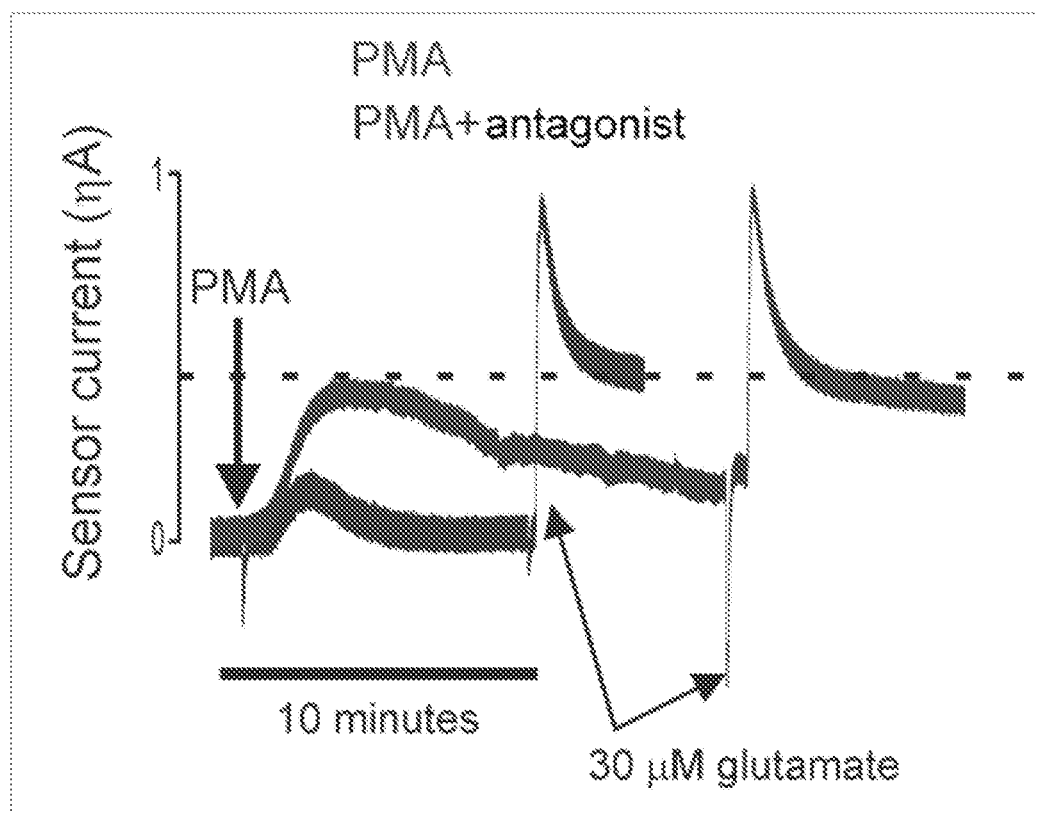
FIG. 1E shows the effects of treating neutrophils with a glutamate antagonist.

In a fifth experiment, as illustrated in FIG. 1E, the effect of a glutamate antagonist was assessed. This experiment was carried out using isolated neutrophils or whole blood from a patient. PMA was added to 1 ml heparinised whole blood with release of ~15 µm glutamate observed (upper line with later glutamate addition in FIG. 1E). In a second population of neutrophils isolated at the same time from the same patient, in the presence of a specific glutamate antagonist (the antagonist was an NR2B antagonist CO101244, 100 µM which was added 1 minute before PMA addition), PMA stimulation of neutrophils failed to increase glutamate release. A null sensor measured non-specific release of oxygen reactive species. The glutamate sensor detects glutamate release in real time. The tips of the sensors were 2 mm under neutrophils in PBS-glucose suspension, maintained at 37° C. Glutamate was added to chamber at the end of experiment (as indicated in FIG. 1E) to calibrate the concentration of glutamate release.

Experiments using ATP Sensor

Samples of whole blood from human patients were analysed using the Sarissagold ATP sensor.

PMA was added to 1 ml heparinised whole blood maintained at 37° C. (as indicated by PMA in FIG. 2). A null sensor measured non-specific release of oxygen reactive species. The ATP sensor detects ATP release in real time. The tips of the sensors were 2 mm under the surface of the blood. ATP was added to chamber at the end of experiment (indicated as 10 µM ATP in FIG. 2) to calibrate amount of ATP release.

Figure 2:
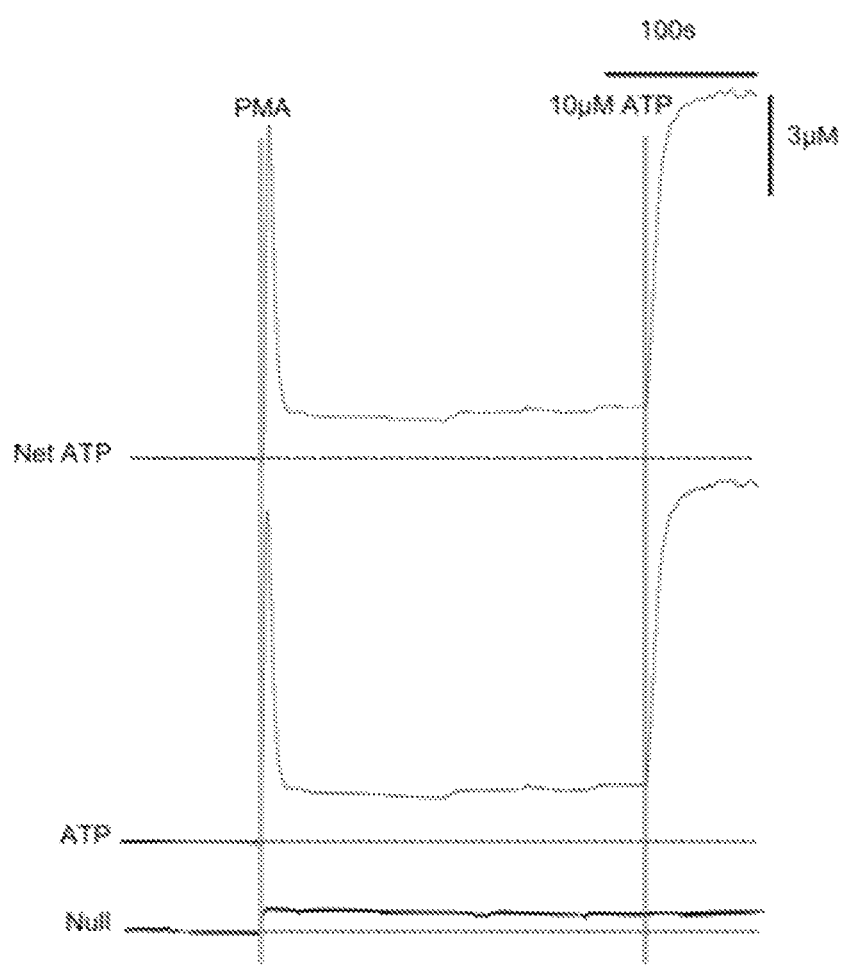
FIGS. 2 to 5 show the effects of treating whole blood with PMA or opsonised *E. coli*.

As shown in FIG. 2, the addition of PMA led to an increase in the response recorded using the ATP sensor.

Experiments using D-Serine Sensor

Samples of whole blood from human patients were analysed using the Sarissagold D-Serine sensor.

PMA was added to 1 ml heparinised whole blood maintained at 37° C. (as indicated by PMA in FIG. 3). A null sensor measured non-specific release of oxygen reactive species. The D-serine sensor detects D-serine release in real time. The tips of the sensors were 2 mm under the surface of the blood. D-serine was added to chamber at the end of the experiment (indicated by 1 µM D-Serine in FIG. 3) to calibrate amount of D-serine release.

Figure 3:
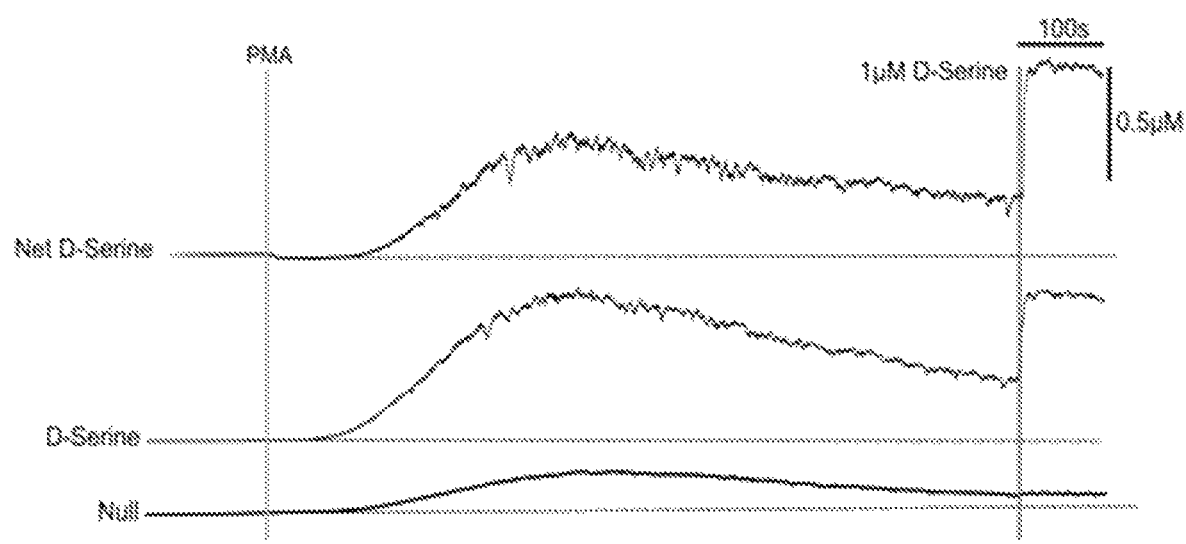

As shown in FIG. 3, the addition of PMA led to an increase in the response recorded using the D-serine sensor.

Experiments using Acetylcholine Sensor

Samples of whole blood from human patients were analysed using the Sarissagold acetylcholine sensor.

PMA was added to 1 ml heparinised whole blood maintained at 37° C. (as indicated by PMA in FIG. 4). A null sensor measured non-specific release of oxygen reactive species. The acetylcholine sensor detects acetylcholine release in real time. The tips of the sensors were 2 mm under the surface of the blood. Acetylcholine was added to chamber at the end of the experiment (Ach in FIG. 4) to calibrate the amount of acetylcholine release.

Figure 4:
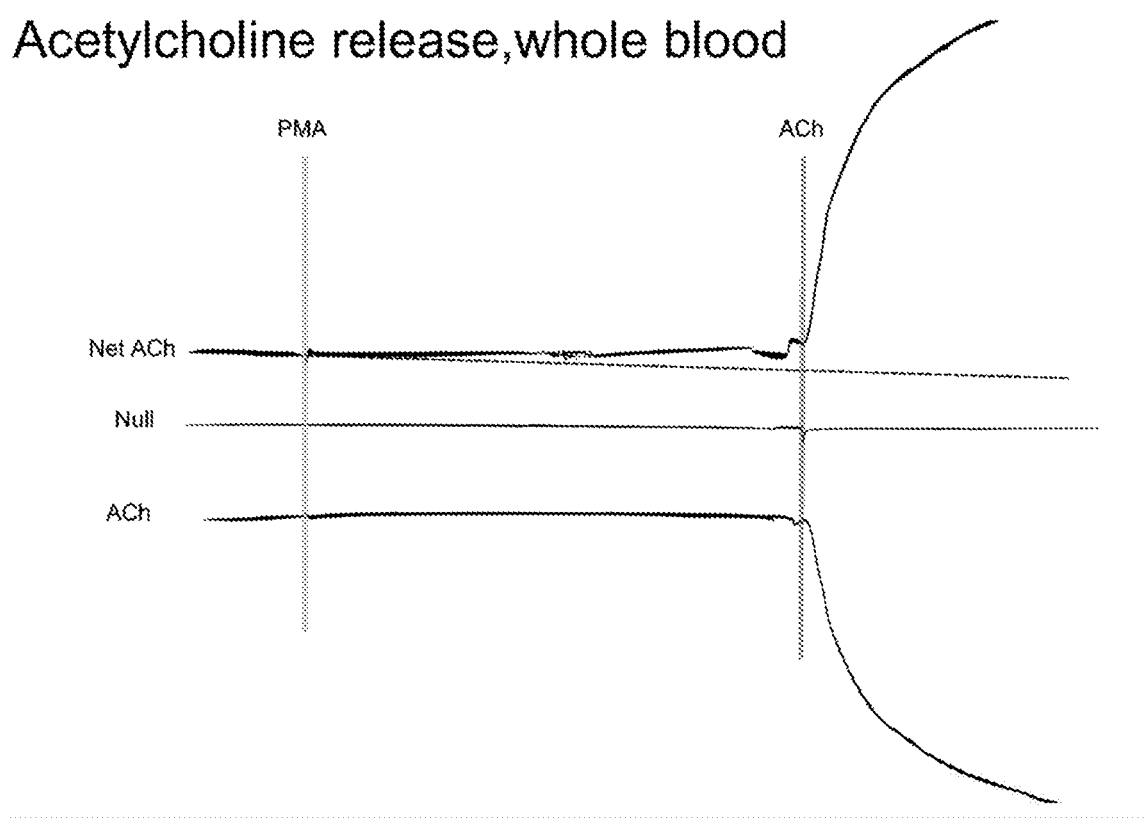

As shown in FIG. 4, the addition of PMA led to an increase in the response recorded using the acetylcholine sensor.

Experiments using Adenosine Sensor

Samples of whole blood from human patients were analysed using the Sarissagold adenosine sensor.

Figure 5:
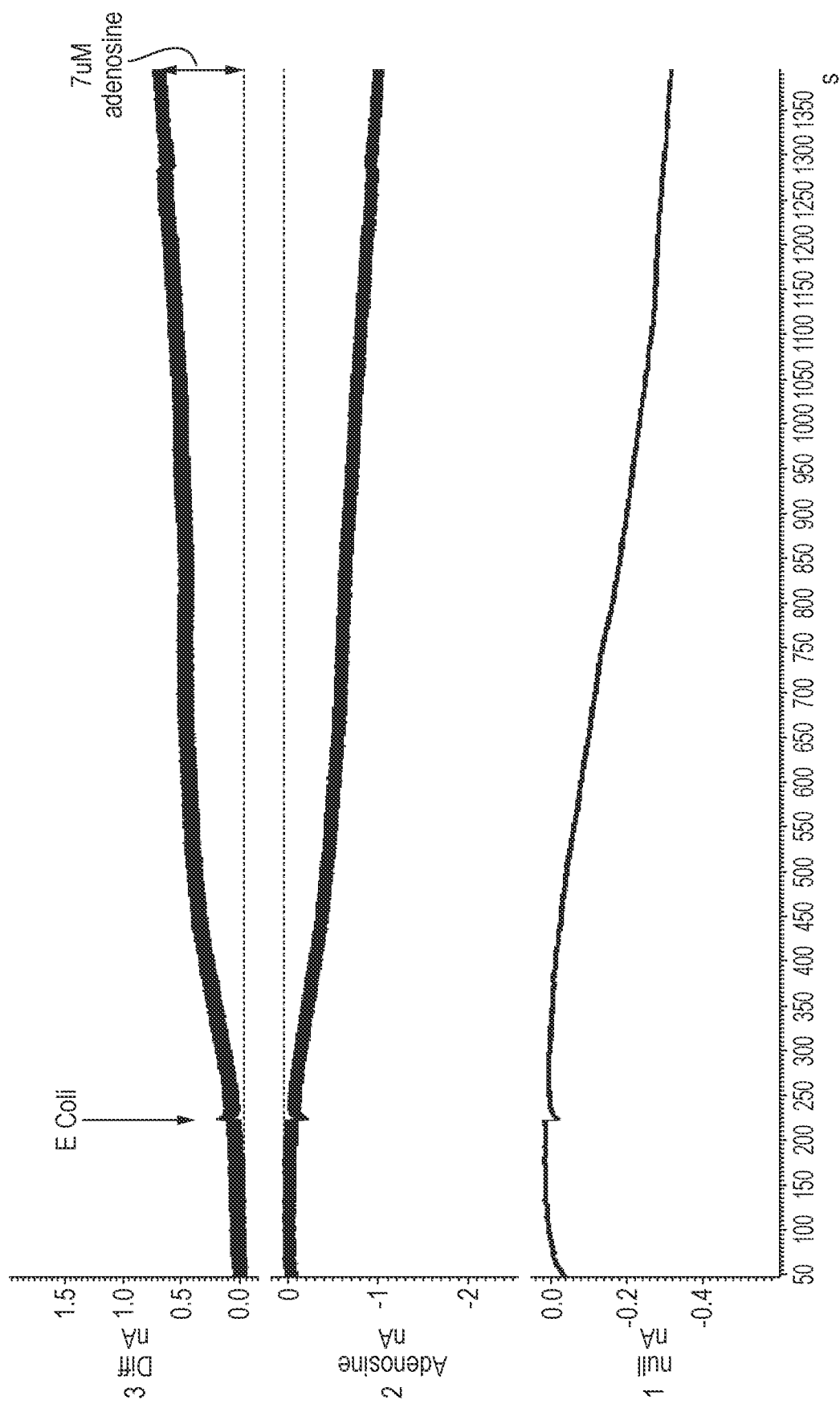

E. coli was added to 1 ml heparinised whole blood maintained at 37° C. (as indicated in FIG. 5). A null sensor measured non-specific release of oxygen reactive species. The adenosine sensor detects adenosine release in real time. The tips of the sensors were 2 mm under the surface of blood.

As shown in FIG. 5, the addition of E. coli led to an increase in the response recorded using the adenosine sensor.

Example 2

Ex-Vivo Rat Model of Inflammation

Materials, instrumentation, microelectrode biosensors and experimental protocol were as for example 1.

Ex-Vivo Experiments

Male Sprague-Dawley rats 100-150 g (n=6/group) were injected with zymosan (500 mg/kg), a yeast wall product that triggers peritoneal inflammation via activation of Toll Like Receptor-2. Naïve (non-injected) rats served as controls. By 48 h, this dose results in at least 60% mortality. An observer masked to the treatments assessed their health— whether they looked unwell—1-2 h after the injection. At this point the rats only show very subtle features of systemic inflammation, typically characterized by mild piloerection of their fur. None of the rats were identified as being sick. Following cervical dislocation, blood was obtained and briefly lysed with red cell lysis buffer, washed with sterile phosphate-buffered saline (PBS), added to 1 ml PBS and then added to a incubation chamber heated to 37° C. Sensors were then inserted into the chamber, separated by at least 5 mm. After at least 2 minutes of stabilization, Phorbol myristate acetate (PMA) was added to the chamber to stimulate the neutrophils in the sample.

Measurements using Glutamate Sensors

Figure 6:
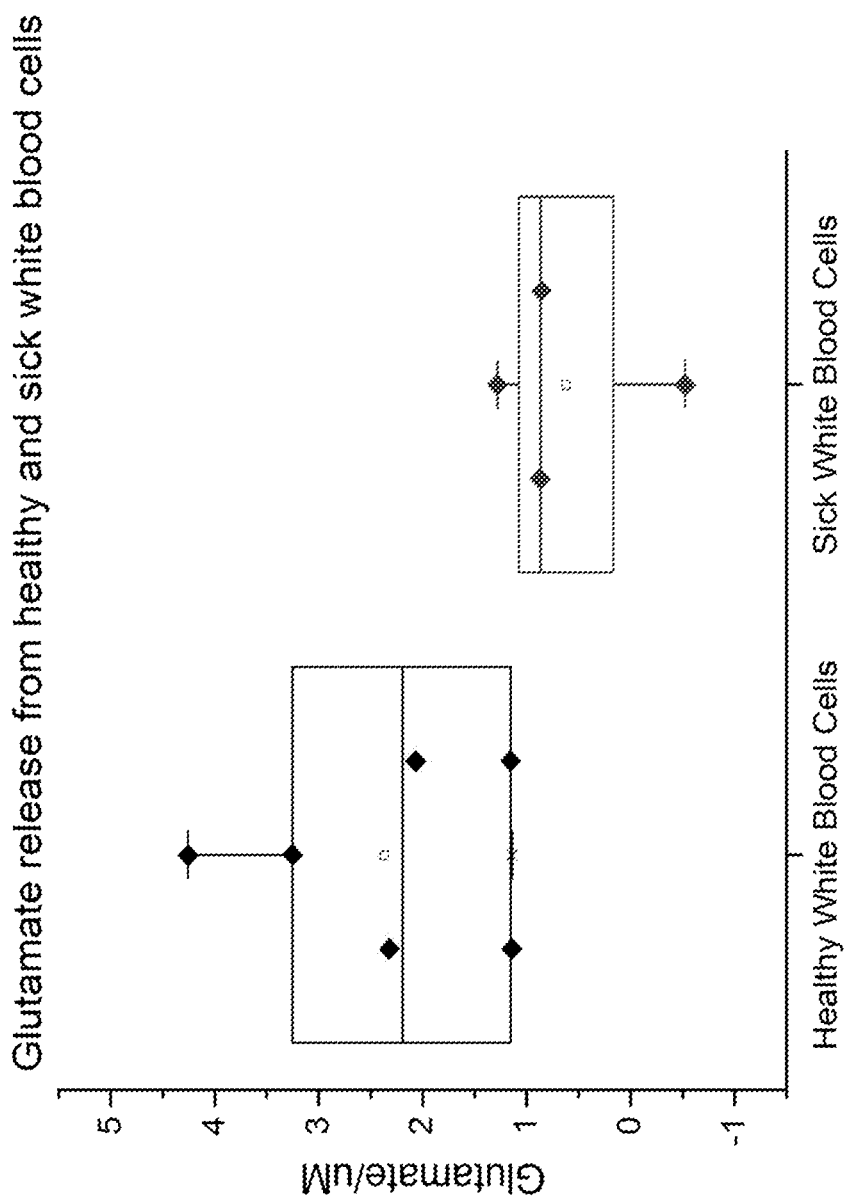
FIGS. 6 and 7 show the effects on neutrophils from blood of rats treated with the inflammatory agent zymosan of stimulation with PMA, compared with the effect on neutrophils from healthy controls.

FIG. 6 shows the change in glutamate concentration in the sample in response to stimulation with PMA for healthy control rats (left) and zymosan-treated 'sick' rats (right). The glutamate concentrations after stimulation were greater than the pre-stimulation concentrations by an amount in the range 1 µM to 4 µM in the healthy rats and by an amount in the range −0.5 µM to 1 µM in the sick rats, and the average response in samples from healthy rats was approximately 2-fold higher than that observed from zymosan-treated rats.

Measurements using Lactate Sensors

Figure 7:
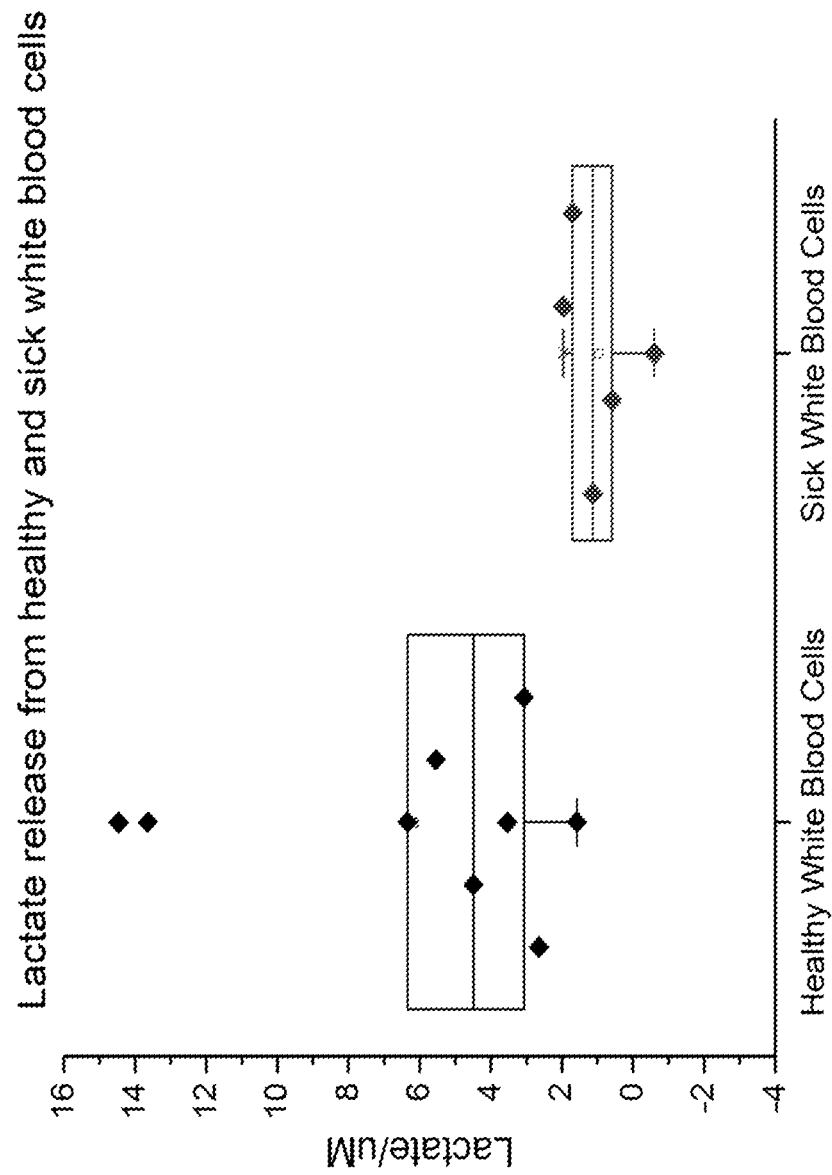

FIG. 7 shows the change in lactate concentration in the sample in response to stimulation with PMA for healthy control rats (left) and zymosan-treated 'sick' rats (right). The lactate concentrations after stimulation were greater than the pre-stimulation concentrations by an amount in the range 1.5 µM to 14.5 µM in the healthy rats and by an amount in the range −0.5 µM to 2 µM in the sick rats, and the average response in samples from healthy rats was approximately 4-fold higher than that observed from zymosan-treated rats.

Discussion

Treatment with zymosan causes inflammation of the epithelial cell lining of the intestine, leading to leakage of (gram negative) bacteria such as *E. coli* from the intestinal lumen into the peritoneal cavity. The test therefore provides an ex-vivo analogue of the in-vitro test with (opsonised) *E. coli* in Example 1. In both examples, the results show that following exposure to *E. coli* (opsonised *E. coli* in Example 1, gut bacteria including *E. coli* in Example 2) the response of neutrophils in whole blood to a stimulant such as PMA, as indicated by the release of a biomarker such as glutamate, is reduced compared to the response of neutrophils in a control sample. As shown in FIGS. 6 and 7, the change in concentration of the biomarkers on stimulation is markedly different between samples from the sick rats and from the healthy rats, allowing a diagnosis to be made of inflammation in the sick rats by the methods of the invention, while the sick rats are not distinguishably different from the healthy rats by observation alone.

The invention claimed is:

1. A method of detecting infection or inflammation in a mammalian subject, the method comprising the steps of:
   (a) detecting an amount of at least one marker selected from the group consisting of glutamate, lactate, ATP, D-serine, acetylcholine and adenosine in an in vitro or ex vivo sample comprising neutrophils from said subject;
      wherein the detection of the marker(s) comprises contacting the sample comprising neutrophils from said subject with one or more biosensors, wherein the biosensor(s) comprises (i) an enzyme capable of recognizing the marker(s) and (ii) an electrode capable of detecting a reaction product caused by the recognition of said marker(s) by the enzyme; and
      wherein the reaction product is hydrogen peroxide;
   (b) further contacting the sample comprising neutrophils from step (a) with a pathogen, or a molecule(s) derived from a pathogen;
   (c) detecting in the sample comprising neutrophils from step (b) an amount of the same marker(s) as detected in step (a) within 5 minutes of contacting the sample comprising neutrophils from step (b) with the pathogen or molecule(s) derived from a pathogen, wherein detection of the marker(s) comprises contacting the sample comprising neutrophils from step (b) with the same biosensor(s) from step (a), and determining a change in the amount of the marker(s) detected as compared to the to the amount of the marker(s) detected in step (a); and
   (d) repeating steps (a) to (c) with an ex vivo or in vitro sample comprising neutrophils from a control, wherein a decrease in the change of said marker(s) from the sample comprising neutrophils from the subject as compared to the change of said marker(s) from the sample comprising neutrophils from the control is indicative of the presence of inflammation or infection in the subject.

2. The method according to claim 1 wherein the control sample is from a normal subject, and the amount of the marker(s) from the control sample is used as a control value.

3. The method according to claim 1 wherein the infection is a pathogenic infection, a bacterial infection, a viral infection, a fungal infection and/or sepsis.

4. The method according to claim 1 wherein said method is used to monitor the relative amounts of said marker(s) in said subject at two or more different points in time.

5. The method according to claim 1 wherein the sample comprising neutrophils from the subject and/or the control is ex vivo and said method is used to monitor changes in the amount of said marker(s) in said subject in real-time.

6. The method according to claim 1 wherein:
   (i) detection of glutamate is carried out using a biosensor comprising glutamate oxidase; or
   (ii) detection of lactate is carried out using a biosensor comprising lactate oxidase, or
   (iii) detection of ATP is carried out using a biosensor comprising glycerol kinase and glycerol-3-phosphate oxidase, or
   (iv) detection of acetylcholine is carried out using a biosensor comprising acetylcholine esterase and choline oxidase, or
   (v) detection of D-serine is carried out using a biosensor comprising D-amino acid oxidase, or
   (vi) detection of adenosine is carried out using a biosensor comprising adenosine deaminase, nucleoside phosphorylase and xanthine oxidase.

7. The method according to claim 1, wherein the control sample is an earlier sample from the subject and a decrease from around 0.5 µM to around 10 µM in the amount of said marker(s) when compared to the amount from the control indicates that the subject has developed an infection or inflammation.

8. The method of claim 1, wherein the decrease in the change of said marker(s) from the sample comprising neutrophils from the subject as compared to the change of said marker(s) from the sample comprising neutrophils from the control is around 0.5 µM to around 6 µM.

9. The method of claim 1, wherein the biosensor further comprises Ruthenium Purple.

10. The method according to claim 6 wherein:
(i) the biosensor comprises glutamate oxidase, wherein said glutamate oxidase catalyses a reaction of glutamate in the sample to form 2-oxoglutarate+$NH_3$+$H_2O_2$, and wherein an electrode in said biosensor detects said production of $H_2O_2$; or
(ii) the biosensor comprises lactate oxidase, wherein said lactate oxidase catalyses a reaction of lactate in the sample to form pyruvate+$H_2O_2$ and wherein an electrode in said biosensor detects said production of $H_2O_2$, or
(iii) the biosensor comprises glycerol kinase and glycerol-3-phosphate oxidase, wherein said glycerol kinase and glycerol-3-phosphate oxidase catalyse a reaction of ATP in the sample to form glycerine phosphate+$H_2O_2$, and wherein an electrode in said biosensor detects said production of $H_2O_2$, or
(iv) the biosensor comprises acetylcholine esterase and choline oxidase, wherein said acetylcholine esterase and choline oxidase catalyse a reaction of acetylcholine in the sample to form betaine aldehyde+$H_2O_2$, and wherein an electrode in said biosensor detects said production of $H_2O_2$, or
(v) the biosensor comprises D-amino acid oxidase, wherein said D-amino acid oxidase catalyses a reaction of D-serine in the sample to form 2-oxo-3-hydroxypropionate+$NH_3$+$H_2O_2$, and wherein an electrode in said biosensor detects said production of $H_2O_2$, or
(vi) the biosensor comprises adenosine deaminase, nucleoside phosphorylase and xanthine oxidase, wherein said adenosine deaminase catalyses a reaction of adenosine to form inosine, said nucleoside phosphorylase catalyses a reaction of inosine to form hypoxanthine and said xanthine oxidase catalyses a reaction of said hypoxanthine to form urate and $H_2O_2$, and wherein an electrode in said biosensor detects said production of $H_2O_2$.

11. The method of claim 6, wherein the biosensor further comprises a layer of Ruthenium Purple on the electrode.

* * * * *